United States Patent
Muñoz Blanco et al.

(10) Patent No.: US 10,919,843 B2
(45) Date of Patent: Feb. 16, 2021

(54) CANNABIDIOL DERIVATIVES AS INHIBITORS OF THE HIF PROLYL HYDROXYLASES ACTIVITY

(71) Applicant: Emerald Health Pharmaceuticals Inc., San Diego, CA (US)

(72) Inventors: Eduardo Muñoz Blanco, Cordova (ES); Carmen María Navarrete Rueda, Cordova (ES); Cristina Cruz Teno, Cordova (ES); María Luz Bellido Cabello De Alba, Cordova (ES)

(73) Assignee: Emerald Health Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 16/498,768

(22) PCT Filed: Mar. 29, 2017

(86) PCT No.: PCT/EP2017/057389
§ 371 (c)(1),
(2) Date: Sep. 27, 2019

(87) PCT Pub. No.: WO2018/177516
PCT Pub. Date: Oct. 4, 2018

(65) Prior Publication Data
US 2020/0087247 A1    Mar. 19, 2020

(51) Int. Cl.
*C07C 225/28*        (2006.01)
(52) U.S. Cl.
CPC ................... *C07C 225/28* (2013.01)
(58) Field of Classification Search
CPC ................................... C07C 225/28
See application file for complete search history.

(56) References Cited

FOREIGN PATENT DOCUMENTS

| EP | 2551255 A1 | 1/2013 |
|---|---|---|
| WO | 2005067917 | 7/2005 |
| WO | 2008107878 A1 | 9/2008 |
| WO | 2015158381 A1 | 10/2015 |

OTHER PUBLICATIONS

Appendino, et al. Document No. 163:618125, retrieved from STN; entered in STN on Oct. 22, 2015.*
SARS [online] retrieved from the internet on May 11, 2020; https://www.emedicinehealth.com/severe_acute_respiratory_syndrome_sars/article_em.htm*
Coronavirus [online] retrieved from the internet on May 11, 2020: https://www.nfid.org/infectious-diseases/coronaviruses/.*
Aragonés et al., "Oxygen Sensors at the Crossroad of Metabolism", Cell Metab., 2009, 9:11-22.
Bruick RK et al., "A Conserved Family of Prolyl-4-Hydroxylases That Modify HIF", Science, 2001. 294:1337-1340.
Del Rio C et al., "The cannabinoid quinol VCE-004.8 alleviates bleomycin-induced scleroderma and exerts potent antifibrotic effects through peroxisome proliferator-activated receptor-[gamma] and CB2 pathways", Scientific Reports, 2016, 6:21703, 14 pages.
Eckle T et al., "HIF1A Reduces Acute Lung Injury by Optimizing Carbohydrate Metabolism in the Alveolar Epithelium", 2013, PLoS Biol. 11, e1001665, 25 pages.
Ehrenreich H et al., "Recombinant Human Erythropoietin in the Treatment of Acute Ischemic Stroke", Stroke 2009 40 (12): e647-e656.
Eltzschig et al., "Targeting hypoxia signalling for the treatment of ischaemic and inflammatory diseases", Nat. Rev. Drug Discov., 2014, 13:852-869.
Eltzschig HK et al., "Hypoxia and Inflammation", P. N. Engl. J. Med., 2011, 364:656-665.
Granja AG et al., "A Cannabigerol Quinone Alleviates Neuroinflammation in a Chronic Model of Multiple Sclerosis", J. Neuroimmune Pharmacol., 2012, 7:1002-1016.
International Search Report and Written Opinion for PCT/EP2017/057389 dated Nov. 16, 2017, 15 pages.
Li W et al., "Beneficial effect of erythropoietin on experimental allergic encephalomyelitis", Ann. Neurol., 2004, 56:767-777.
Peng et al., "The efficacy of erythropoietin in treating experimental traumatic brain injury: a systematic review of controlled trials in animal models", J. Neurosurg. 2014. 121:653-664.
Philips JA et al., "Matrix metalloproteinase activity synergizes with a2h1 integrins to enhance collagen remodeling", Exp. Cell Res., 2005, 310:79-87.
Rabinowitz MH, "Inhibition of Hypoxia-Inducible Factor Prolyl Hydroxylase Domain Oxygen Sensors: Tricking the Body Into Mounting Orchestrated Survival and Repair Responses", J. Med. Chem., 2013, 56: 9369-9402.
Ratcliffe PJ, "HIF-1 and HIF-2: working alone or together in hypoxia?", J. Clin. Invest. 2007, 17:862-865.
Semenza et al., "Transcriptional Regulation of Genes Encoding Glycolytic Enzymes by Hypoxia-inducible Factor 1", J. Biol. Chem., 1994, 269:237357-23763.

(Continued)

*Primary Examiner* — Shawquia Jackson
(74) *Attorney, Agent, or Firm* — Riverside Law LLP

(57) ABSTRACT

Cannabidiol quinol derivatives of Formula (I) and compositions comprising the same for use in the treatment of conditions that benefit from the inhibition of the HIF prolyl hydroxylases (PHDs) activity are described. Said cannabidiol quinol derivatives of Formula (I), and compositions comprising the same, show thus capacity to inhibit PHD activities and, as a result, stabilize the HIF-1α and HIF-2α levels, activate the HIF pathway in different cell types, induce angiogenesis in human endothelial vascular cell, regulate HIF-dependent gene expression in different cell types and induce collagen contraction. Said cannabidiol quinol derivatives of Formula (I) are useful in the treatment of conditions that benefit from the inhibition of the HIF prolyl hydroxylases (PHDs) activity such as stroke, traumatic injuries anemia, myocardial ischaemia-reperfusion injury, acute lung injury, infectious diseases, diabetic and chronic wounds, organ transplantation, acute kidney injury or arterial diseases.

6 Claims, 9 Drawing Sheets
Specification includes a Sequence Listing.

(56) References Cited

OTHER PUBLICATIONS

Solinas M et al., "Cannabidiol, a Non-Psychoactive Cannabinoid Compound, Inhibits Proliferation and Invasion in U87-MG and T98G Glioma Cells through a Multitarget Effect", PLoS One, 2013, 8:e76918, 9 pages.

Speer et al., "Hypoxia-inducible factor prolyl hydroxylases as targets for neuroprotection by "antioxidant" metal chelators: From ferroptosis to stroke", Free Radic. Biol. Med., 2013, 62:26-36.

Sun YY et al., "Glucocorticoid Protection of Oligodendrocytes against Excitotoxin Involving Hypoxia-Inducible Factor-1a in a Cell-Type-Specific Manner", J. Neurosci., 2010, 30:9621-9630.

Takeda et al., "Essential Role for Prolyl Hydroxylase Domain Protein 2 in Oxygen Homeostasis of the Adult Vascular System", Circulation, 2007, 116:774-781.

Wang GL et al., "Oxygen sensing and response to hypoxia by mammalian cells", Redox Rep. ,1996, 2:89-96.

Wu et al., 2012, The protective role of hypoxic preconditioning in CNS, Anoxia, Dr. Pamela Padilla (Ed.), InTech, DOI: 10.5772/27621, 18 pages.

Yan L et al., "Prolyl hydroxylase domain-containing protein inhibitors as stabilizers of hypoxia-inducible factor: Small molecule-based therapeutics for anemia", Expert Opin Ther Pat., 2010, 20:1219-1245.

Yang YT et al., "Induction of hypoxia inducible factor-1 attenuates metabolic insults induced by 3-nitropropionic acid in rat C6 glioma cells", J. Neurochem., 2005, 96: 513-525.

\* cited by examiner

A

B

A

B

C

A

B

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: EPO primer forward

<400> SEQUENCE: 1
ctccgaacaa tcactgct                                                      18

<210> SEQ ID NO 2
<211> LENGTH: 20
<212> TYPE: DNA
<213> ORGANISM: Artificial Sequence
<220> FEATURE:
<223> OTHER INFORMATION: EPO primer reverse

<400> SEQUENCE: 2
ggtcatctgt cccctgtcct                                        20

<210> SEQ ID NO 3
<211> LENGTH: 23
<212> TYPE: DNA
<213> ORGANISM: Artificial Sequence
<220> FEATURE:
<223> OTHER INFORMATION: VEGFA primer forward

<400> SEQUENCE: 3
cgaagtggtg aagttcatgg atg                                    23

<210> SEQ ID NO 4
<211> LENGTH: 23
<212> TYPE: DNA
<213> ORGANISM: Artificial Sequence
<220> FEATURE:
<223> OTHER INFORMATION: VEGFA primer reverse

<400> SEQUENCE: 4
ttctgtatca gtctttcctg gtg                                    23

<210> SEQ ID NO 5
<211> LENGTH: 22
<212> TYPE: DNA
<213> ORGANISM: Artificial Sequence
<220> FEATURE:
<223> OTHER INFORMATION: GAPDH primer forward

<400> SEQUENCE: 5
tggcaaagtg gagattgttg cc                                     22

<210> SEQ ID NO 6
<211> LENGTH: 21
<212> TYPE: DNA
<213> ORGANISM: Artificial Sequence
<220> FEATURE:
<223> OTHER INFORMATION: GAPDH primer reverse

<400> SEQUENCE: 6
aagatggtga tgggcttccc g                                      21

CANNABIDIOL DERIVATIVES AS INHIBITORS OF THE HIF PROLYL HYDROXYLASES ACTIVITY

CROSS-REFERENCE TO RELATED APPLICATIONS

The present application is a 35 U.S.C. § 371 national phase application from International Application PCT/EP2017/057389, filed on Mar. 29, 2017, the disclosure of which is incorporated herein by reference in its entirety.

FIELD OF THE INVENTION

The present invention relates to the use of cannabidiol quinol derivatives of Formula (I) for use in the treatment of diseases benefiting from the inhibition of HIF prolyl hydroxylases (PHDs). Particularly as HIF prolyl hydroxylases inhibitors, said compounds stabilize the levels of the HIF-1α and HIF-2α proteins, which results in the activation of the HIF-1 pathway. The inhibition of PHDs induces angiogenesis and collagen contraction which is useful in conditions such as anemia, myocardial ischaemia-reperfusion injury, acute lung injury, infectious diseases, diabetic and chronic wounds, organ transplantation, acute kidney injury or arterial diseases. This invention also provides pharmaceutical compositions comprising said compounds for treating said diseases.

BACKGROUND OF THE INVENTION

Mammalian cells need to maintain proper oxygen homeostasis in order to execute their aerobic metabolism and energy generation. Since the discovery of the hypoxia-inducible factor (HIF)-1, signaling mechanisms underlying oxygen-sensing by HIF transcription factors have been extensively studied in biological contexts (Wang et al., Redox Rep. 1996, 2:89-96). HIFs, composed of oxygen-labile α and constitutively expressed β subunits, drive the transcription of numerous genes involved in diverse cellular processes including erythropoiesis, angiogenesis, energy metabolism, ischemia, and inflammation (Semenza et al., J. Biol. Chem. 1994, 269:237357-63 and Eltzschig et al., Nat. Rev. Drug Discov. 2014, 13:852-69). HIF is present in cells almost exclusively in two forms: HIF-1 and HIF-2. They are heterodimeric transcription factors consisting of a constitutively produced highly abundant HIF-β subunit and either a HIF-1α or HIF-2α partner, in the case of HIF-1 and HIF-2, respectively, sharing 48% sequence homology (Rabinowitz M H, J. Med. Chem. 2013, 56: 9369-4025). HIF-1 is frequently associated with metabolic and vascular responses to hypoxia, whereas HIF-2 is associated with vascular systems but also with erythropoiesis (Ratcliffe P J. J. Clin. Invest. 2007, 17:862-5).

The mechanism by which oxygen controls HIF-1α has been revealed by the identification of HIF prolyl hydroxylases (PHDs) (Bruick and McKnight, Science 2001, 294 (5545):1337-40). Under normoxia, PHD hydroxylates proline residues in the oxygen dependent degradation domain of HIF-1α, thereby allowing binding to von Hippel Lindau protein (pVHL)-elongin B-elongin C, leading to active ubiquitination and degradation with a half-life of approximately 5 min. In contrast, the oxygen deprivation under hypoxia (lack of oxygen in the cells) impairs hydroxylation of HIF-1α, by PHDs, resulting in reduced HIF-1α degradation, increased HIF-1α stabilization and subsequent induction of a plethora of target genes including vascular endothelial growth factor (VEGF)-A and erythropoietin (EPO) genes. (Rabinowitz M H, J. Med. Chem. 2013, 56(23):9369-4025). PHDs belong to the family of the dioxygenase enzymes that require oxygen, iron, and 2-oxyglutarate (2-OG) for their catalytic activity. Three PHD isoforms (PHD1, PHD2, and PHD3) have been identified, and their substrates are known to be quite diverse and isoform-specific (Rabinowitz M H, J. Med. Chem. 2013, 56:9369-4025 and; Eltzschig et al., Nat. Rev. Drug Discov. 2014, 11:852-69).

PHD2 is considered critical in regulating the HIF pathway. Specifically, enhanced angiogenesis, and increased levels of VEGF-A and EPO were observed in conditional knockout of PHD2 (Takeda et al., Circulation 2007, 116: 774-81). Such observations, along with reports showing that HIF enhanced EPO release and concomitantly increased erythropoiesis, imply that activation of HIF by modulating PHDs could be beneficial for patients with anemia and ischemia-related diseases. Accordingly, pharmacological approaches to manipulate the HIF pathway by inhibiting PHD activity have been pursued to treat systemic and local hypoxia-related diseases (Rabinowitz M H, J. Med. Chem. 2013, 56: 9369-4025 and; Eltzschig et al., Nat. Rev. Drug Discov. 2014, 13:852-69).

Neuronal damage secondary to brain injuries such as cerebral hypoxia, is a complex process. The activation of a common mechanism related to survival or cell death, mediated by the stabilization and trans-activation of HIF-1α, has been observed in these conditions. PHDs are the gatekeepers for the oxygen-dependent degradation of HIF-1α and also function as integrated sensors of cellular metabolism (Aragonts et al., Cell Metab. 2009, 9:11-22). The phenomenon that hypoxic preconditioning (HP) protects against subsequent severe anoxia was discovered approximately two decades ago. Subsequently, the effects of HP have been studied intensively in vitro and in vivo hypoxic models. Although the exact mechanisms are not completely disclosed, the underlying molecular mechanisms have been postulated. For example, HP activates a great variety of endogenous protective mediators including stabilization of the HIF-1α and HIF-2α levels, increasing the capability of cell survival under severe oxygen deprivation (Wu et al., 2012. The protective role of hypoxic preconditioning in CNS. Anoxia. Dr. Pamela Padilla (Ed.), InTech. DOI: 10.5772/27621).

Some of the diseases where hypoxia in the brain occurs include stroke, traumatic injuries etc. Until now, there are no any effective drugs to protect the brain from these diseases. Disclosure of the mechanism of HP will contribute to drug discovery for prevention against said diseases. A number of cellular adaptive responses to hypoxia are mediated by HIF-1α and activation of this factor by HP enhances the capability to tolerate severe anoxia or ischemia. The target genes of HIF-1, on the one hand, are involved in energy homeostasis, such as EPO in the regulation of erythropoiesis, vascular endothelial growth factor (VEGF) in angiogenesis, glucose transmitters (GLUTs) in glucose uptake and glycolytic enzymes of anaerobic glycolysis (Speer et al., Free Radio. Biol. Med. 2013, 62:23-36). Moreover, activation of HIF-1α in oligodendrocytes has been reported to induce EPO, which confers protection in oligodendrocytes against excitotoxicity (Sun et al., J. Neurosci. 2010, 30:9621-30). In this sense the benefit of EPO in several diseases such as, stroke, demyelinating diseases and traumatic brain injuries has been also demonstrated (Peng et al., J. Neurosurg. 2014, 1:653-64; Ehrenreich et al., Stroke 2009 40 (12): e647-56; Li et al., Ann. Neurol. 2004, 56:767-77).

In addition, hypoximimetic agents such as desferrioxamine (DFX) protect neuronal insults induced by 3-nitropoionic acid (Yang et al., J. Neurochem. 2005, 96: 513-25). Therefore, PHDs inhibition by hypoximetic small-molecules represents an interesting strategy or the development of therapies for the clinical management of conditions where hypoxia occurs, such as stroke, or traumatic injuries.

A substantial number of pharmacological studies (generally using nonspecific PDH2 inhibitors) have been conducted in animal models, and a few clinical studies have been performed. Indeed, several companies are involved in the discovery and development of PHD inhibitors for anemia and other indications such as IBD, myocardial ischaemia-reperfusion injury, acute lung injury, infectious diseases, diabetic and chronic wounds, organ transplantation, acute kidney injury and arterial diseases are areas in which PHD inhibitors are actively being pursued by many researchers as a novel therapeutic approach (Rabinowitz M H, J. Med. Chem. 2013, 56:9369-4025 and; Eltzschig et al., Nat. Rev. Drug Discov. 2014, 13:852-69). In addition it has been shown that PDH inhibitors influence wound healing and tissue remodeling and collagen gel model systems are used to measure functional outputs associated with tissue remodeling (Philips et al., Exp Cell Res. 2005: 310:79-87).

The original description of HIF-selective PHDs as regulators of HIF expression has provided a template for the development of PHD-based molecular tools and therapies. Pharmacological inactivation of the PHDs by 2-OG analogues is sufficient to stabilize HIF-1α, but this action is nonspecific with respect to individual PHD isoforms and in vitro studies showed that the oxygen degradation domain sequence of HIF-1α is hydroxylated most efficiently by PHD2 (Rabinowitz M H, J. Med. Chem. 2013, 56:9369-4025). These observations have generated considerable interest in identifying enzyme-modifying small-molecule inhibitors. Indeed, several PHD inhibitor classes have been described, including iron chelators such as DFX, hydralazine, AKB-4924, FG-2229, TM-6008 and 1-mimosine; CUL2 deneddylators such as MLN4924; 2-OG mimics such as ximethyloxalylglycine and N-oxalyl-d-phenylalanine; PHD active-site blockers such as pyrazolopyridines, 8-hydroxyquinolines, compound A. FG-4497 and TM-6089; and $Fe^{2+}$ substitutes such as $Co^{2+}$, $Ni^{2+}$ and $Cu^{2+}$. The mechanism of action of these compounds is based on the observation that the binding of the co-substrate 2-00 to the catalytic domain, which harbors an essential $Fe^{2+}$ ion, is crucial for enzymatic PHD2 activity. Therefore, chemical compounds that structurally mimic 2-OG, such as N-oxalylglycine or its precursor DMOG (dimethyloxaloylglycine), inhibit PHD2 by blocking the entry of the co-substrate (Rabinowitz M H, J. Med. Chem. 2013, 56:9369-4025 and: Eltzschig et al., Nat. Rev. Drug Discov. 2014, 13:8.52-69).

Cannabidiol (CBD) is a phytocannabinoid derived from *Cannabis* species, which is devoid of psychoactive activity, with analgesic, anti-inflammatory, antineoplastic and chemopreventive activities. Upon administration, cannabidiol (CBD) exerts its anti-proliferative and pro-apoptotic activity through various mechanisms, which likely do not involve signaling by cannabinoid receptor type 1 (CB1) and cannabinoid receptor type 2 (CB2). In addition. CBD is a weak agonist of PPARγ (Granja et al., J. Neuroimmune Pharmacol. 2012, 7:1002-16) CBD inhibits cancer cell invasiveness and metastasis and also inhibits the hypoxia-induced stabilization of HIF-1α (Solinas et al., PLoS One. 2013, 8(10): e76918) a and is a weak activator of the nuclear receptor PPARγ. In contrast, some CDB quinol derivatives showed a stronger binding and capacity of activation of this nuclear receptor (del Rio et al., Sci Rep. 2016, 6:21703) (Vivacell Biotechnology España, S. L. 2015. Novel Cannabidiol quinone derivatives. WO2015158381A1).

DETAILED DESCRIPTION

Departing from the prior art, it is the problem of the present invention to provide compounds with exhibit activity inhibiting the HIF prolyl hydroxylases (PHDs) and as a consequence result in the stabilization of the HIF-1α and HIF-2α levels, and induce HIF-dependent transcriptional activities. It is thus the problem of present invention to provide compounds for use in the treatment of conditions that benefit from the inhibition of the PHDs activity.

Although Cannabidiol (CBD), as mentioned above, inhibits the stabilization of HIF-1α, the applicant has found surprisingly that some CBD quinol derivatives are inhibitors of the PHDs activity, and thus stabilize the HIF-1α and HIF-2α levels, instead of inhibiting its stabilization as the CBD precursor does.

More specifically, the present invention relates to compounds (CBD-Q derivatives) of Formula (I):

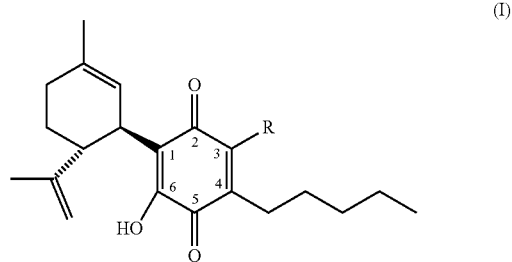

wherein R is the carbon atom of a group independently selected from aryl, linear or branched alkenyl, linear or branched alkynyl, acyl, or alkoxycarbonyl groups; or wherein R is the nitrogen atom of a group independently selected from a linear or branched alkylamine, an arylamine, a linear or branched alkynylamine or a linear or branched alkynylamine, for use in the treatment of conditions that benefit from the inhibition of the HIF prolyl hydroxylases (PHDs) activity.

Those compounds of Formula (I), and compositions comprising the same, are thus inhibitors of PHDs, and as a result said compounds and compositions show capacity to stabilize the levels of the HIF-1α and HIF-2α proteins, activate the HIF pathway in different cell types, induce angiogenesis in human endothelial vascular cell, induce the expression of HIF-1-dependent genes and mediate collagen contraction. Said compounds of Formula (I) are thus useful in the treatment of conditions that benefit from the inhibition of the HIF prolyl hydroxylases (PHDs) activity.

The inhibition of the PHDs activity, results in the stabilization of the levels of HIF-1α and HIF-1β, which in turn increases the capability of cell survival under oxygen deprivation or hypoxia. The conditions that benefit from the inhibition of the PHDs activity, are thus conditions in which hypoxia (lack oxygen in the cells) occurs, and thus, conditions in which the stabilization of the HIF-1α and HIF-1β levels is advantageous for its treatment. When lack of oxygen (hypoxia) occurs, a temporary biological response activates the HIF pathway. Said temporary response is often not long enough to repair and avoid the damages created in the organism by the aforesaid hypoxia. The compounds disclosed in present invention, by inhibiting the activity of PHDs, are able to mimic the response of the body in the event of hypoxia, stabilizing the levels of the HIF proteins and activating the HIF pathway, which in turn induces angiogenesis, wound healing and/or the expression of genes involved in the protection of cell damage caused by the lack of oxygen present in hypoxia.

Therefore, the inhibition of PHDs induces the expression of HIF-dependent genes, angiogenesis and collagen contraction, which are useful in conditions such as anemia, myocardial ischaemia-reperfusion injury, acute lung injury, infectious diseases, diabetic and chronic wounds, organ transplantation, acute kidney injury or arterial diseases.

For the purposes of present invention, said conditions that benefit from the inhibition of the HIF prolyl hydroxylases (PHDs) activity comprise but are not limited to stroke, traumatic injuries, anemia, myocardial ischaemia-reperfusion injury, acute lung injury, infectious diseases, diabetic and chronic wounds, organ transplantation, acute kidney injury or arterial diseases.

For the purpose of present description stroke refers to a neurological deficit of cerebrovascular cause. Strokes can be classified in two major categories: ischemic and hemorrhagic. Ischemic strokes are caused by interruption of the blood supply to the brain, while hemorrhagic strokes result from the rupture of a blood vessel or an abnormal vascular structure. In both cases, a stroke results in a situation of hypoxia in brain cells, due to the interruption of the normal supply of oxygen to the brain. Pharmacological activation of the HIF pathway enhances the expression of genes whose products can protect neuronal cells from the damage caused by acute hypoxia events.

For the purposes of present description traumatic injuries refer to physical injuries of sudden onset and severity, which require immediate medical attention. Traumatic injuries are the result of a wide variety of blunt, penetrating and burn mechanisms. Said traumatic injuries include motor vehicle collisions, sports injuries, falls, natural disasters and a multitude of other physical injuries. In those events, the injuries often result in the interruption of the blood supply to the cells, and thus result in a situation of hypoxia, due to the interruption of the normal supply of oxygen through the blood vessels. The inhibition of the PHDs activity, and as a result the activation of the HIF pathway, enhances the production of Vascular Endothelial Growth Factor (VEGF) that in turn increases the formation of new blood vessels that enhances oxygen supply to the tissues.

For the purposes of present description anemia refers to a decrease in the total amount of red blood cells or of hemoglobin in the blood. This affects the amount of oxygen supply in cells resulting in a situation of hypoxia. The inhibition of the PHDs activity and, as a result, the activation of the HIF pathway enhances the production of erythropoietin (EPO) that in turn increases the production of red blood cells.

For the purposes of present description myocardial ischaemia-reperfusion injury refers to the tissue damage caused when blood supply returns to the tissue after a period of myocardial ischemia or lack of oxygen (anoxia, hypoxia). The inhibition of the PHDs activity and, as a result, the activation of the HIF pathway induces cardioprotection by ischaemic preconditioning. Ischaemic preconditioning is an experimental strategy whereby pre-exposure to short, non-lethal episodes of ischaemia results in attenuated myocardial tissue injury during subsequent ischaemia-reperfusion injury.

For the purposes of present description acute lung injury refers to a condition that is characterized by acute severe hypoxia and where its diagnosis is based on the presence of non-cardiogenic pulmonary oedema and respiratory failure in a critically ill patient. The inhibition of the PHDs activity and, as a result, the activation of the HIF pathway in mice was associated with dramatic increases in survival during acute lung injury induced by mechanical ventilation (Eckle. T. et al. 2013. PLoS Biol. 11, e1001665).

For the purposes of present description infectious diseases refer to diseases caused by pathogenic microorganisms, such as bacteria, viruses, parasites or fungi, and wherein said diseases can be spread, directly or indirectly, from one person to another. The inhibition of the PHDs activity and, as a result, the activation of the HIF pathway has been implicated in the function of myeloid cells to clear infections. Not only is HIF1 essential to support glycolytic metabolism of phagocytes, but it also regulates key functions such as bacterial uptake, production of antimicrobial effector molecules and enhancing longevity of neutrophils (Eltzschig, H. K, and Carmeliet, P. N. Engl. J. Med. 2011, 364, 656-665).

For the purposes of present description diabetic and chronic wounds refer to wounds, which may be caused by a diabetic condition, that do not heal in an orderly set of stages and in a predictable amount of time the way most wounds do. In general, wounds that do not heal within three months are often considered chronic. The inhibition of the PHDs activity and, as a result, the stabilization of the HIF levels results in (1) enhanced angiogenesis which promotes healing, and (2) collagen contraction which also influences wound healing and tissue remodeling.

For the purposes of present description acute kidney injury refers an abrupt loss of kidney function from numerous causes that develops within 7 days. Said abrupt loss of kidney function causes damage to the kidney tissue and it is generally caused by decreased renal blood flow (renal ischemia).

For the purposes of present description on organ transplantation several studies suggest that HIF activators can prevent early graft failure during solid organ transplantation, such as heart, kidney, lung or liver transplantation. Other studies indicate that ischaemia and reperfusion also have important immunological consequences in organ transplantation, such as affecting the severity of early liver rejection (Eltzschig et al., Nat. Rev. Drug Discov. 2014, 13:852-69).

For the purposes of present description arterial diseases include a class of diseases that involve ischaemia in peripheral arteries and chronic vascular occlusion. Ischaemia normally induces the production of angiogenic cytokines and the homing of bone-marrow-derived angiogenic cells, but these adaptive responses become impaired with ageing because of reduced expression of HIFs. Activation of the HIF pathway increased perfusion, motor function and limb salvage in old mice subjected to femoral artery ligation. Similarly, a different study provided strong evidence that mice with genetic deletion of Phd1 are protected during hindlimb ischaemia as a result of increased HIF levels Eltzschig et al., Nat. Rev. Drug Discov. 2014, 13:852-69).

In a preferred embodiment, R is the nitrogen of a group independently selected from a linear or branched alkylamine, an arylamine, a linear or branched alkynylamine or a linear or branched alkynylamine In a preferred embodiment, R is the nitrogen atom of a linear alkylamine. In another preferred embodiment, R is the nitrogen atom of a branched alkylamine. In another preferred embodiment, R is the nitrogen atom of a arylamine.

Those compounds of Formula (I) show thus capacity to:
inhibit the activity of PHDs. i.e., said compounds inhibit the hydroxylation of the HIF proteins by PHDs, as shown in Example 2 disclosed below herein,
activate the HIF pathway, as shown in Example 1 disclosed below herein.
stabilization of HIF proteins levels, as shown in Example 2 disclosed below herein,
induce angiogenesis in human endothelial vascular cells, as shown in Example 3 disclosed below herein,
induce the expression of HIF-1α-dependent genes, as shown in Example 4 disclosed below herein,
induce collagen contraction, as shown in Example 5 disclosed below herein.

The inhibition of the hydroxylase activity of PHDs, and as a result, the stabilization of the levels of HIF-1α and HIF-2α proteins, mimics the situation where the oxygen deprivation under hypoxia impairs the hydroxylation of HIF-1α, by PHDs, activating the HIF pathway.

Present invention also comprises the derivatives of the compounds of Formula (I), and compositions containing the same for use in the treatment of conditions that benefit from the inhibition of the HIF prolyl hydroxylases (PHDs) activity. Said derivatives of the compounds of Formula (I) refer to the tautomeric forms, isomers, stereoisomers, polymorphs, esters, pharmaceutically acceptable salts or pharmaceutically acceptable solvates. In a more preferred embodiment said derivatives of the compounds of Formula (I) refer to the pharmaceutically acceptable salts thereof.

The term "tautomers" are constitutional isomers of organic compounds that readily interconvert by a chemical process (tautomerization).

The term "isomers" or "stereoisomers" refers to compounds, which have identical chemical constitution, but differ with regard to the arrangement of the atoms or groups in space.

As used herein "polymorph" refers to crystalline forms having the same chemical composition but different spatial arrangements of the molecules, atoms, and/or ions forming the crystal.

The term "pharmaceutically acceptable salt" refers to any pharmaceutically acceptable salt, which upon administration to the patient is capable of providing (directly or indirectly) a compound as described herein. Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts. However, it will be appreciated that non-pharmaceutically acceptable salts also fall within the scope of the invention since those may be useful in the preparation of pharmaceutically acceptable salts. Procedures for salt formation are conventional in the art.

The term "solvate" in accordance with this invention should be understood as meaning any form of the active compound in accordance with the invention in which said compound is bonded by a non-covalent bond to another molecule (normally a polar solvent), including especially hydrates and alcoholates.

In a preferred embodiment of present invention, the compounds of Formula (I) for use in the treatment of conditions that benefit from the inhibition of the HIF prolyl hydroxylases (PHDs) activity are those of Formula (II), (III), (IV), (V), (VI), (VII), (VIII), (X) and (XI):

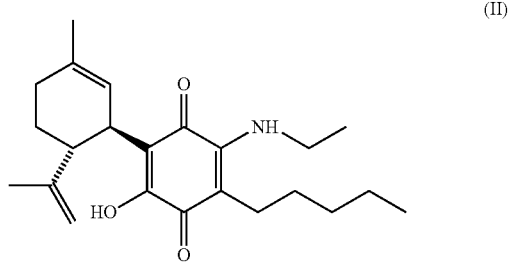

(1'R,6'R)-3-(Ethylamine)-6-hydroxy-3'-methyl-4-pentyl-6'-(prop-1-en-2-yl)-[1,1'-bi(cyclohexane)]-2',3,6-triene-2,5-dione (II)

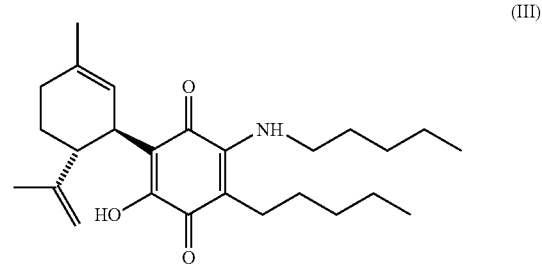

(1'R,6'R)-3-(Pentylamine)-6-Hydroxy-3'-methyl-4-pentyl-6'-(prop-1-en-2-yl)-[1,1'-bi(cyclohexane)]-2',3,6-triene-2,5-dione (III)

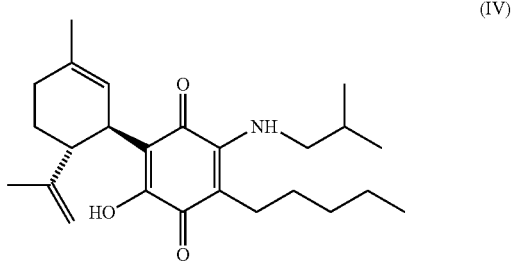

(1'R,6'R)-3-(Isobutylamine)-6-Hydroxy-3'-methyl-4-pentyl-6'-(prop-1-en-2-yl)-[1,1'-bi(cyclohexane)]-2',3,6-triene-2,5-dione (IV)

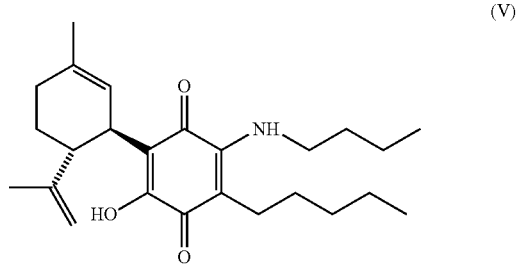

(1'R,6'R)-3-(Butylamine)-6-hydroxy-3'-methyl-4-pentyl-6'-(prop-1-en-2-yl)-[1,1'-bi(cyclohexane)]-2',3,6-triene-2,5-dione (V)

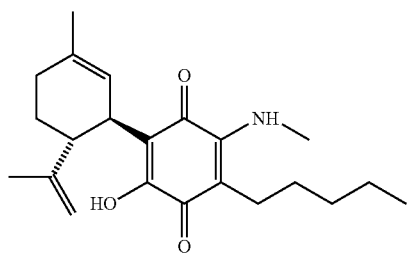

(1'R,6'R)-3-(Methylamine)-6-Hydroxy-3'-methyl-4-pentyl-6'-(prop-1-en-2-yl)-[1,1'-bi(cyclohexane)]-2',3,6-triene-2,5-dione

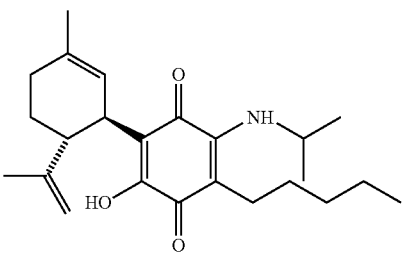

(1'R,6'R)-3-(Isopropylamine)-6-Hydroxy-3'-methyl-4-pentyl-6'-(prop-1-en-2-yl)-[1,1'-bi(cyclohexane)]-2',3,6-triene-2,5-dione

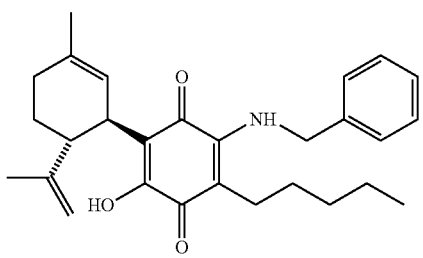

(1'R,6'R)-3-(Benzylamine)-6-hydroxy-3'-methyl-4-pentyl-6'-(prop-1-en-2-yl)-[1,1'-bi(cyclohexane)]-2',3,6-triene-2,5-dione

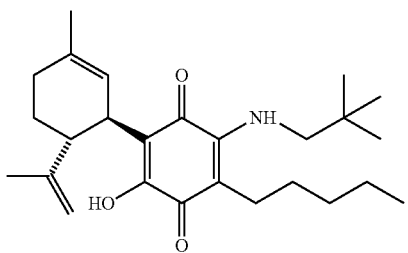

(1'R,6'R)-3-(Neopentylamine)-6-hydroxy-3'-methyl-)-4-pentyl-6'-(prop-1-en-2yl)-[1,1'-bi(cyclohexane)]-2',3,6-triene-2,5-dione

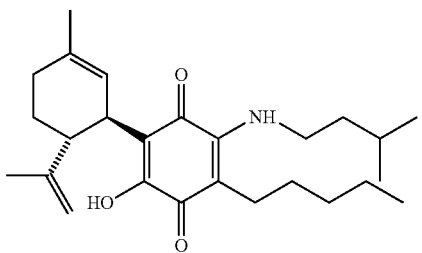

(1'R,6'R) 3-(Isopentylamine)-6-Hydroxy-amine-3'-methyl-4-pentyl-6'-(prop-1-en-2-yl)-[1,1'-bi(cyclohexane)]-2',3,6-triene-2,5-dione VCE-004 is the precursor of the compounds of Formula II to X for use according to present invention can be easily synthesized from CBD (THC Pharma, Germany; ref: THC-1073G-10) (del Rio et al., Sci Rep. 2016, 6:21703 and WO2015158381A1).

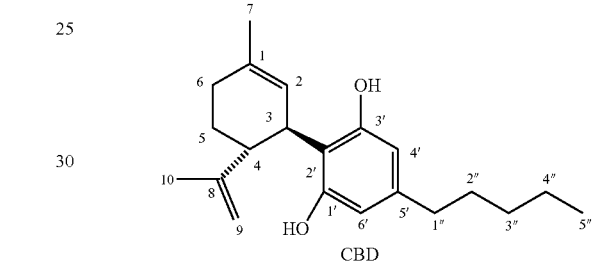

CBD

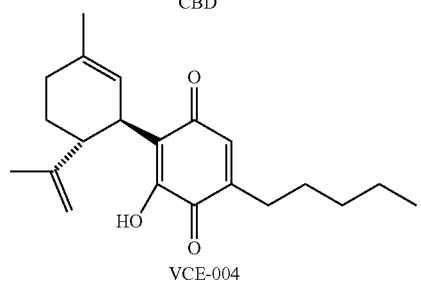

VCE-004

As it will be inferred below from the examples and figures, the modifications in position 3' comprised in the general Formula I confer the compounds of the present invention the capacity to activate the HIF pathway, and are therefore compounds useful in the treatment of conditions that benefit from the inhibition of the HIF prolyl hydroxylases (PHDs) activity.

Importantly, neither CBD or VCE-004 (known CBD derivative which features no substitution at said position 3 of the quinol ring) activate the HIF pathway, demonstrating that the specific modifications at position 3 of the quinol rings of VCE-004 are critical to inhibit the HIF prolyl hydroxylases (PHDs) activity, as shown by the CBD derivatives of Formula (I) described in the present invention.

As shown in the examples and figures of present description, the modifications comprised in the compounds of general Formula (I) confer the compounds disclosed herein with the capacity to inhibit the activity of PHDs, and as a result said compounds stabilize the levels of HIF-1α and HIF-2α proteins, activate the HIF pathway in different cell types, induce angiogenesis in human endothelial vascular cells, induce the expression of different HIF-1α-dependent genes, and increase collagen contraction.

One embodiment of present invention relates to the compounds of general Formula (I), as described above herein, or to any of the compounds of Formula (II), (III), (IV), (V), (VI), (VII), (VIII), (X) and (XI), for use in the treatment of conditions that benefit from the inhibition of the HIF prolyl hydroxylases (PHDs) activity, wherein said conditions are independently selected from stroke, traumatic injuries, myocardial ischaemia-reperfusion injury, acute lung injury, infectious diseases, diabetic and chronic wounds, organ transplantation, acute kidney injury or arterial diseases.

A preferred embodiment refers to the compounds of general Formula (I), as described above herein, or to any of the compounds of Formula (II), (III), (IV), (V), (VI), (VII), (VIII), (X) and (XI), for use in the treatment of conditions that benefit from the inhibition of the HIF prolyl hydroxylases (PHDs) activity, wherein said conditions are independently selected from stroke, myocardial ischaemia-reperfusion injury, acute lung injury, diabetic and chronic wounds, acute kidney injury or arterial diseases.

An embodiment disclosed herein refers to compositions, particularly pharmaceutical compositions, comprising at least a compound of Formula (I) or derivative thereof,

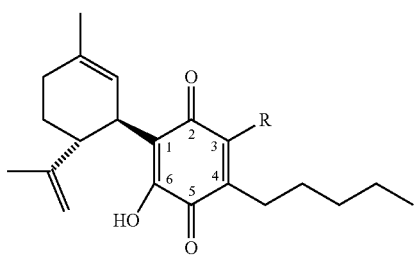

(I)

wherein R is the carbon atom of a group independently selected from aryl, linear or branched alkenyl, linear or branched alkynyl, acyl, or alkoxycarbonyl groups; or wherein R is the nitrogen atom of a group independently selected from a linear or branched alkylamine, an arylamine, a linear or branched alkynylamine or a linear or branched alkynylamine, and at least one excipient or carrier, for use in the treatment of conditions that benefit from the inhibition of the HIF prolyl hydroxylases (PHDs) activity.

In a preferred embodiment said derivatives of the compounds of Formula (I) refer to the tautomeric forms, isomers, stereoisomers, polymorphs, esters, pharmaceutically acceptable salts or pharmaceutically acceptable solvates. In a more preferred embodiment said derivatives of the compounds of Formula (I) refer to the pharmaceutically acceptable salts thereof.

Said excipient or carrier refers, for the purpose of present invention, to an inert ingredient such as, but not limited to, cosolvents, surfactants, oils, humectants, emollients, preservatives, stabilizers and antioxidants. Any pharmacologically acceptable buffer may be used, such as TRIS or any phosphate buffer.

Typical compositions for use, according to present invention, include the compounds of Formula (I), or derivatives thereof, described above herein associated with pharmaceutically acceptable excipients, which may be a carrier or a diluent, as a way of example. Such compositions can be in the form of a capsule, sachet, paper or other container. In making the compositions, conventional techniques for the preparation of pharmaceutical compositions may be used. For example, the compounds of Formula (I) disclosed above herein may be mixed with a carrier, or diluted by a carrier, or enclosed within a carrier that may be in the form of an ampoule, capsule, sachet, paper, or other container. When the carrier serves as a diluent, it may be solid, semi-solid, or liquid material that acts as a vehicle, excipient, or medium for the active compound. The compounds of Formula (I) and compositions comprising the same, for use as described above herein can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. Said compositions may also include wetting agents, emulsifying and suspending agents, preserving agents, sweetening agents or flavouring agents. The compositions for use in the treatment of conditions that benefit from the inhibition of the HIF prolyl hydroxylases (PHDs) activity, described in present invention may be formulated so as to provide quick, sustained, or delayed release of the compounds of Formula (I) disclosed herein after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the compounds disclosed above herein.

Another embodiment disclosed herein refers to compositions, particularly pharmaceutical compositions, wherein said compositions comprise any of the compounds of Formula (I) selected from (II), (III), (IV), (V), (VI), (VII), (VIII), (IX) or (X).

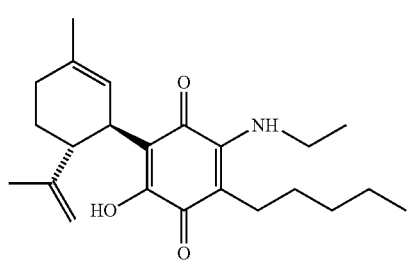

(II)

(1'R,6'R)-3-(Ethylamine)-6-hydroxy-3'-methyl-4-pentyl-6'-(prop-1-en-2-yl)-[1,1'-bi(cyclohexane)]-2',3,6-triene-2,5-dione -continued

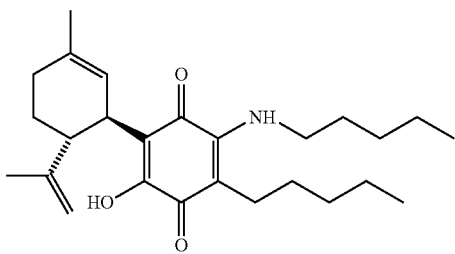

(1′R,6′R)-3-(Pentylamine)-6-Hydroxy-3′-methyl-4-pentyl-6′-(prop-1-en-2-yl)-[1,1′-bi(cyclohexane)]-2′,3,6-triene-2,5-dione (IV)

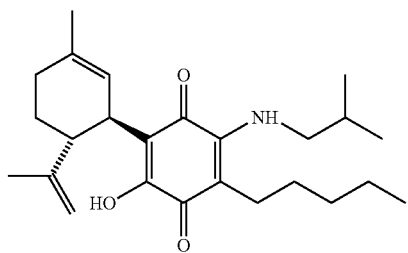

(1′R,6′R)-3-(Isobutylamine)-6-Hydroxy-3′-methyl-4-pentyl-6′-(prop-1-en-2-yl)-[1,1′-bi(cyclohexane)]-2′,3,6-triene-2,5-dione (V)

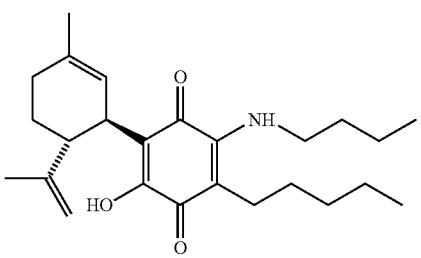

(1′R,6′R)-3-(Butylamine)-6-hydroxy-3′-methyl-4-pentyl-6′-(prop-1-en-2-yl)-[1,1′-bi(cyclohexane)]-2′,3,6-triene-2,5-dione (VI)

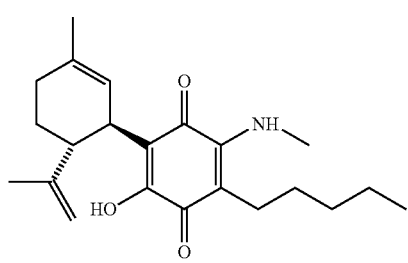

(1′R,6′R)-3-(Methylamine)-6-Hydroxy-3′-methyl-4-pentyl-6′-(prop-1-en-2-yl)-[1,1′-bi(cyclohexane)]-2′,3,6-triene-2,5-dione -continued (VII)

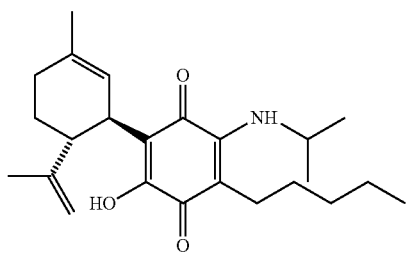

(1′R,6′R)-3-(Isopropylamine)-6-Hydroxy-3′-methyl-4-pentyl-6′-(prop-1-en-2-yl)-[1,1′-bi(cyclohexane)]-2′,3,6-triene-2,5-dione (VIII)

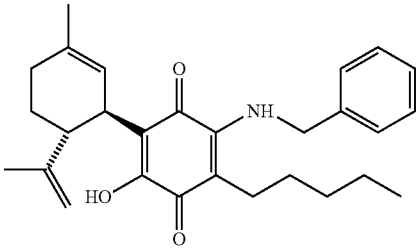

(1′R,6′R)-3-(Benzylamine)-6-hydroxy-3′-methyl-4-pentyl-6′-(prop-1-en-2-yl)-[1,1′-bi(cyclohexane)]-2′,3,6-triene-2,5-dione (IX)

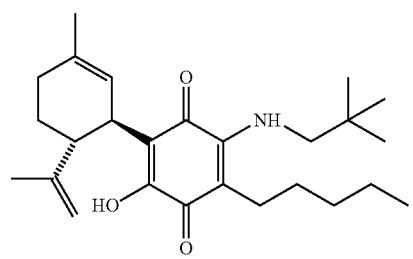

(1′R,6′R)-3-(Neopentylamine)-6-hydroxy-3′-methyl-)-4-pentyl-6′-(prop-1-en-2yl)-[1,1′-bi(cyclohexane)]-2′,3,6-triene-2,5-dione (X)

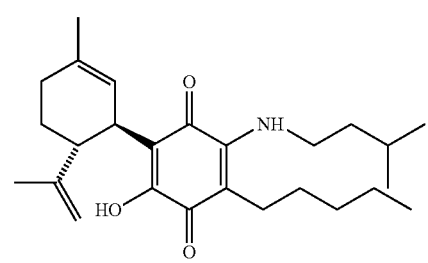

(1′R,6′R) 3-(Isopentylamine)-6-Hydroxy-amine-3′-methyl-4-pentyl-6′-(prop-1-en-2-yl)-[1,1′-bi(cyclohexane)]-2′,3,6-triene-2,5-dione for use in the treatment of conditions that benefit from the inhibition of the HIF prolyl hydroxylases (PHDs) activity.

The above mentioned compositions, show thus capacity to inhibit the activity of PHDs, and as a result stabilize the levels of HIF-1α and HIF-2α proteins, activate the HIF pathway in different cell types, induce angiogenesis in human endothelial vascular cell, induce the expression of HIF-1-dependent genes, and induce collagen contraction.

Another embodiment disclosed herein refers to the pharmaceutical compositions comprising at least one cannabidiol derivative of Formula (I), (II), (III), (IV), (V), (VI), (VII), (VIII), (IX) or (X), or derivatives thereof, for use in the treatment of conditions that benefit from the inhibition of the HIF prolyl hydroxylases (PHDs) activity, wherein said conditions are independently selected from stroke, traumatic injuries, anemia, myocardial ischaemia-reperfusion injury, acute lung injury, infectious diseases, diabetic and chronic wounds, organ transplantation, acute kidney injury or arterial diseases. Said compositions may further comprise another active ingredient which exerts therapeutic effects when administered to human or animal beings.

The route of administration for said pharmaceutical compositions for use, may be any route which effectively transports the compound of Formula (I) or derivatives thereof, disclosed above herein, to the appropriate or desired site of action, such as oral, nasal, topical, pulmonary, transdermal or parenteral, e.g., rectal, subcutaneous, intravenous, intraurethral, intramuscular, intranasal, ophthalmic solution or an ointment.

For nasal administration, the compositions may contain the compound of Formula (I) or derivatives thereof, disclosed above herein, dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine), or cyclodextrin, or preservatives such as parabens.

To prepare topical compositions, the compound of Formula (I) or derivatives thereof, disclosed above herein, is placed in a dermatological vehicle as is known in the art. The amount of the compound of Formula (I) or derivatives thereof, disclosed above herein to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the compound of Formula (I) or derivatives thereof, disclosed above herein, and selects the amount of formulation administered, depending upon clinical experience with the patient in question or with similar patients.

For ophthalmic applications, the compound of Formula (I) or derivatives thereof, disclosed above herein, is formulated into solutions, suspensions, and ointments appropriate for use in the eye. The concentrations are usually as discussed above herein for local preparations.

For oral administration, either solid or fluid unit dosage forms can be prepared. For preparing solid compositions such as tablets, the compound of Formula (I) or derivatives thereof, disclosed above herein, is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers.

Capsules are prepared by mixing the compound of Formula (I) or derivatives thereof, disclosed above herein with an inert pharmaceutical diluent, and filling the mixture into a hard gelatin capsule of appropriate size. Soft gelatin capsules are prepared by machine encapsulation of slurry of the compound of Formula (I) with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate compositions for parenteral use are apparent to the practitioner of ordinary skill, such as the use of suitable injectable solutions or suspensions. The composition, which is sterile, is suitable for various topical or parenteral routes including intra-dermal, intramuscular, intravascular, and subcutaneous.

In addition to the compound of Formula (I) or derivatives thereof, disclosed above herein, the compositions may include, depending on the composition and mode of delivery desired, pharmaceutically-acceptable, non-toxic carriers or diluents, which include vehicles commonly used to form pharmaceutical compositions for animal or human administration. The diluents are selected so as not to unduly affect the biological activity of the combination.

Examples of such diluents that are especially useful for injectable formulations are water, the various saline, organic or inorganic salt solutions, Ringer's solution, dextrose solution, and flank's solution. In addition, the pharmaceutical composition or formulation may include additives such as other carriers; adjuvants: or non-toxic, non-therapeutic, non-immunogenic stabilizers and the like.

Furthermore, excipients can be included in the compositions disclosed. Examples include but are not limited to cosolvents, surfactants, oils, humectants, emollients, preservatives, stabilizers and antioxidants. Any pharmacologically acceptable buffer may be used, such as, tris or phosphate buffers. Effective amounts of diluents, additives, and excipients are those amounts that are effective to obtain a pharmaceutically acceptable formulation in terms of solubility, biological activity, etc.

The pharmaceutical compositions comprising the compound of Formula (I) or derivatives thereof, disclosed above herein may be incorporated into a microsphere. The compound of Formula (I) or derivatives thereof, disclosed above herein can be loaded into albumin microspheres, from which it is possible to recover such microspheres in a dry powder for nasal administration. Other materials suitable for the preparation of microspheres include agar, alginate, chitosan, starch, hydroxyethyl starch, albumin, agarose, dextran, hyaluronic acid, gelatin, collagen, and casein. The microspheres can be produced by various processes known to the person skilled in the art such as a spray drying process or an emulsification process.

For example, albumin microspheres can be prepared by adding rabbit serum albumin in phosphate buffer to olive oil with stirring to produce water in oil emulsion. Glutaraldehyde solution is then added to the emulsion and the emulsion stirred to cross-link the albumin. The microspheres can then be isolated by centrifugation, the oil removed and the spheres washed, e.g., with petroleum ether followed by ethanol. Finally, the microspheres can be sieved and collected and dried by filtration.

Starch microspheres can be prepared by adding a warm aqueous starch solution, e.g. of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurred in a solvent such as ethanol, after which the particles are again filtered off and laid to dry in air. The microspheres can be hardened by well-known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative.

Another preferred embodiment of the invention is the dosage scheme of the compounds of Formula (I) or derivatives thereof, and of the compositions comprising said compounds, for use in the treatment of conditions that benefit from the inhibition of the HIF prolyl hydroxylases (PHDs) activity, as described above herein. The term "unit dosage form" refers to physically discrete units suitable as unitary dosages for subjects, e.g., mammalian subjects, e.g. humans, dogs, cats, and rodents, each unit containing a predetermined quantity of active material calculated to produce the desired pharmaceutical effect in association with the required pharmaceutical diluent, carrier or vehicle. The specifications for the unit dosage forms are dictated by and dependent on (a) the unique characteristics of the compound of Formula (I) or derivatives thereof, disclosed above herein and the particular effect to be achieved and (b) the limitations inherent in the art of compounding said compound of Formula (I) for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions for use, disclosed herein can be included in kits, which can contain one or more-unit dosage forms of the composition and instructions for use to treat one or more of the diseases described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

An effective amount of the compound of Formula (I) or derivatives thereof, as described above herein, is comprised in the compositions for use in the treatment of conditions that benefit from the inhibition of the HIF prolyl hydroxylases (PHDs) activity, as described in the present invention. The effective amount of the compounds for use, in accordance with the invention varies depending on the compound and the condition being treated for example the age, weight, and clinical condition of the recipient patient. Other factors include: the route of administration, the patient, the patient's medical history, the severity of the disease process, and the potency of the particular compound. The effective amount is an amount sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

One embodiment disclosed herein refers to a method of treating a subject suffering from a condition that benefits from the inhibition of the HIF prolyl hydroxylases (PHDs) activity, comprising administering to said subject an effective amount of any of the compounds of Formula (I) or derivatives thereof,

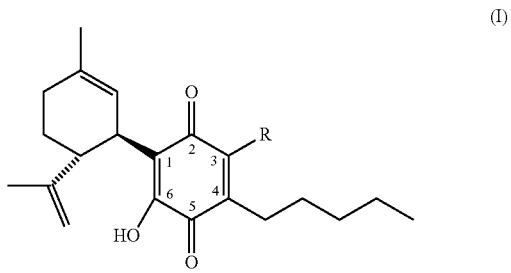

(I)

wherein R is the carbon atom of a group independently selected from aryl, linear or branched alkenyl, linear or branched alkynyl, acyl, or alkoxycarbonyl groups; or wherein R is the nitrogen atom of a group independently selected from a linear or branched alkylamine, an arylamine, a linear or branched alkynylamine or a linear or branched alkynylamine, or a composition, particularly a pharmaceutical composition, comprising the same.

In a preferred embodiment, said method of treating a subject suffering from a condition that benefits from the inhibition of the HIF prolyl hydroxylases (PHDs) activity, comprises administering to said subject an effective amount of any of the compounds of Formula (I) independently selected from (II), (III), (IV), (V), (VI), (VII), (VIII), (IX) or (X):

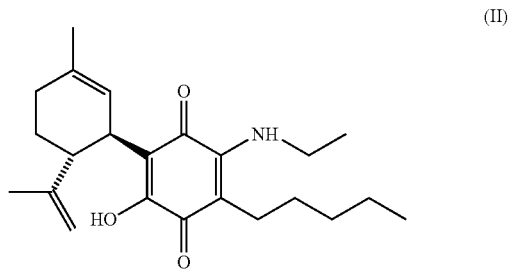

(II)

(1'R,6'R)-3-(Ethylamine)-6-hydroxy-3'-methyl-4-pentyl-6'-(prop-1-en-2-yl)-[1,1'-bi(cyclohexane)]-2',3,6-triene-2,5-dione

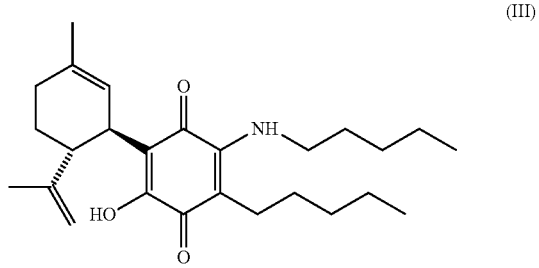

(III)

(1'R,6'R)-3-(Pentylamine)-6-Hydroxy-3'-methyl-4-pentyl-6'-(prop-1-en-2-yl)-[1,1'-bi(cyclohexane)]-2',3,6-triene-2,5-dione

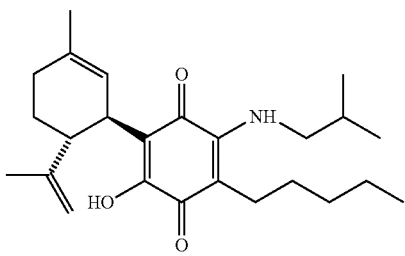

(1′R,6′R)-3-(Isobutylamine)-6-Hydroxy-3′-methyl-4-pentyl-6′-(prop-1-en-2-yl)-[1,1′-bi(cyclohexane)]-2′,3,6-triene-2,5-dione (IV)

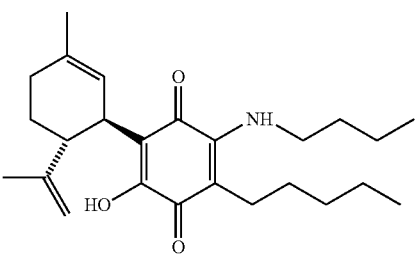

(1′R,6′R)-3-(Butylamine)-6-hydroxy-3′-methyl-4-pentyl-6′-(prop-1-en-2-yl)-[1,1′-bi(cyclohexane)]-2′,3,6-triene-2,5-dione (V)

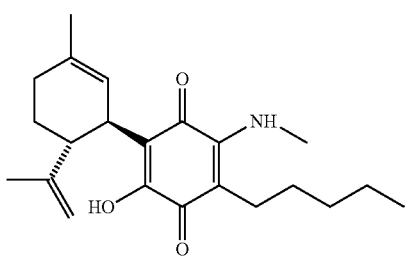

(1′R,6′R)-3-(Methylamine)-6-Hydroxy-3′-methyl-4-pentyl-6′-(prop-1-en-2-yl)-[1,1′-bi(cyclohexane)]-2′,3,6-triene-2,5-dione (VI)

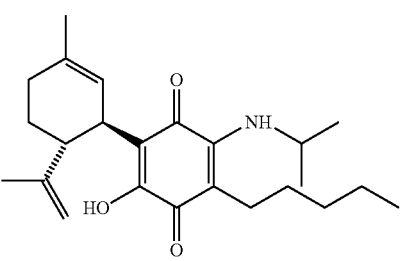

(1′R,6′R)-3-(Isopropylamine)-6-Hydroxy-3′-methyl-4-pentyl-6′-(prop-1-en-2-yl)-[1,1′-bi(cyclohexane)]-2′,3,6-triene-2,5-dione (VII)

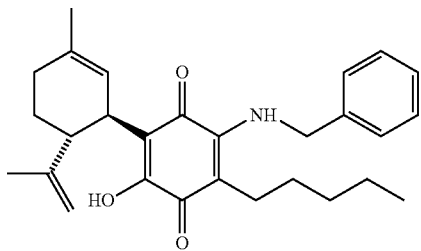

(1′R,6′R)-3-(Benzylamine)-6-hydroxy-3′-methyl-4-pentyl-6′-(prop-1-en-2-yl)-[1,1′-bi(cyclohexane)]-2′,3,6-triene-2,5-dione (VIII)

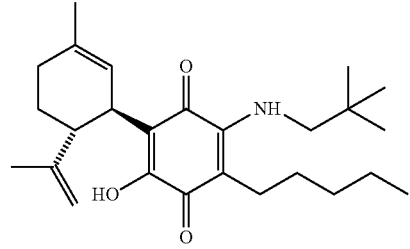

(1′R,6′R)-3-(Neopentylamine)-6-hydroxy-3′-methyl-)-4-pentyl-6′-(prop-1-en-2yl)-[1,1′-bi(cyclohexane)]-2′,3,6-triene-2,5-dione (IX)

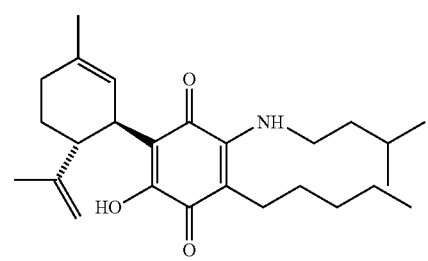

(1′R,6′R) 3-(Isopentylamine)-6-Hydroxy-amine-3′-methyl-4-pentyl-6′-(prop-1-en-2-yl)-[1,1′-bi(cyclohexane)]-2′,3,6-triene-2,5-dione (X)

or a composition comprising the same.

Another embodiment disclosed herein refers to a method of treating a subject suffering from a condition that benefits from the inhibition of the HIF prolyl hydroxylases (PHDs) activity, comprising administering to said subject an effective amount of any of the compounds of Formula (I), (II), (III), (IV), (V), (V), (VII), (VIII), (IX) or (X), or derivatives thereof, or a composition, particularly a pharmaceutical composition, comprising the same, wherein said condition is independently selected from stroke, traumatic injuries, anemia, myocardial ischaemia-reperfusion injury, acute lung injury, infectious diseases, diabetic and chronic wounds, organ transplantation, acute kidney injury or arterial diseases.

BRIEF DESCRIPTION OF THE FIGURES

FIG. 2A shows the stimulation of MO3.13 cells with increasing concentrations of compound VIII or with DFX (150 µM) during 6 h. The steady state levels of the proteins HIF-1α and α-tubulin were determined by Western blots. FIG. 2B shows the time course induction of HIF-1α stabilization in MO3.13 cells stimulated with 2.5 µM compound VIII or 150 µM DFX (1 to 12 hours). The steady state levels of the proteins HIF-1α and α-tubulin were determined by Western blots.

FIG. 5A: Stimulation of HMECs with increasing concentrations of compound VIII or with DFX (150 µM) during 3 hours. The steady state levels of the proteins HIF-1α and α-tubulin were determined by Western blots. FIG. 5B: Time course induction of HIF-1α stabilization in HMEC stimulated with 2.5 µM of compound VIII or 150 µM of DFX. The steady state levels of the proteins HIF-1α and α-tubulin were determined by Western blots. FIG. 5C: The stabilization of the levels of HIF-1α and HIF-2t induced by compound VIII without affecting the expression of PHDs in HMEC. HMEC were stimulated with increasing concentrations of compound VIII or 150 µM of DFX for six hours. The steady state levels of the proteins HIF-1α, HIF-2α, PHD1, PHD2, PDH3, and actin were determined by Western blots.

FIG. 9A: Images of contracted of gel matrices in response to either compound VIII (1, 2.5 and 5 µM) or DMGO for 24h are shown. FIG. 9B: Gel surface area quantified in terms of total pixel number using ImageJ, where indicated * p<0.025 and ** p<0.01.

EXAMPLES

Figure 1:
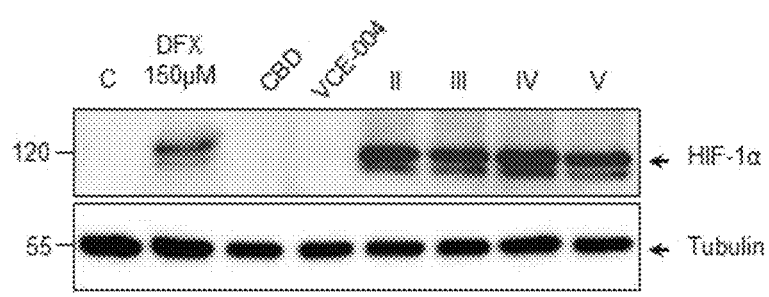
FIG. 1. Cannabidiol derivatives of Formula (I) Induce HIF-1α level stabilization in oligodendrocytes. Stimulation of human oligodendrocyte MO13.3 cells for 6 hours with either 150 of μDFX or 1 μM of Cannabidol (CBD), of VCE-004, of compounds II, III, IV or V (FIG. 1A), or of compounds VI, VII, VIII, IX or X (FIG. 1B), to determine the expression of HIF-1α and α-tubulin by Western blots.
Figure 1:
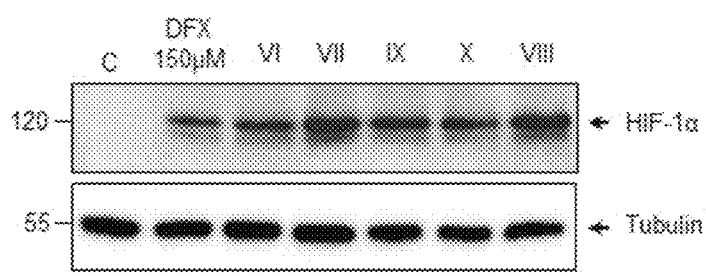

The examples of the present invention described below aim to illustrate its embodiments without limiting its scope of protection.

Example 1. Activation of the HIF Pathway

To investigate the biological activities of the different compounds, HIF-1α transactivation assays were performed either in NIH-3T3-EPO-Luc cells (Table 1) or in HaCaT-EPO-luc cells (Table 2). The NIH3T3-EPO-luc and HaCaT-EPO-luc cells have been stably transfected with the plasmid Epo-Luc plasmid. The EPO-Hypoxia Response Element (HRE)-luciferase reporter plasmid contains three copies of the HRE consensus sequence from the promoter of the erythropoietin gene fused to the luciferase gene.

NIH3T3-EPO-luc cells were maintained at 37° C. in a humidified atmosphere containing 5% $CO_2$ in DMEM supplemented with 10% fetal calf serum (FBS), and 1% (v/v) penicillin/streptomycin. Deferoxamine (DFX) was purchased from Sigma-Aldrich (USA). Cells ($1 \times 10^4$/well in 96-well plates) were seeded the day before the assay. The next day, the cells were stimulated with increasing concentrations of either Cannabidiol (CBD), VCE-004 or compounds II to X. After six hours of stimulation the cells were lysed in 25 mM Tris-phosphate pH 7.8, 8 mM $MgCl_2$, 1 mM DTT, 1% Triton X-100, and 7% glycerol during 15 min at RT in a horizontal shaker. Luciferase activity was measured using a microplate luminometer (Berthold) following the instructions of the luciferase assay kit (Promega, Madison. Wis., USA).

HaCaT-EPO-Luc cells were maintained at 37° C. in a humidified atmosphere containing 5% $CO_2$ in DMEM supplemented with 10% fetal calf serum (FBS), and 1% (v/v) penicillin/streptomycin. The cells ($1 \times 10^5$/well in 24-well plates) were seeded the day before the assay and then stimulated with increasing concentrations of either Cannabidiol (CBD), VCE-004 or compounds II to X. After six hours of stimulation the cells were lysed in 25 mM Tris-phosphate pH 7.8, 8 mM $MgCi_2$, 1 mM DTT, 1% Triton X-100, and 7% glycerol during 15 min at RT in a horizontal shake. Luciferase activity was measured in the cell lysates as indicated for NIH3T3-EPO-Luc cells. The RLUs are calculated and the EC50 and IRA (Intrinsic relative activity) values in both cell lines were determined relative to 150 µM deferoxamine (DFX) using the following equation: IRA coefficient=$(EC_{50\text{-}DFX} \times E_{max})/(EC_{50} \times E_{max\text{-}DFX})$, where $EC_{50}$ and $E_{max}$ denote $EC_{50}$ and $E_{max}$ of the agonist, and $EC_{50\text{-}DFX}$ and $E_{max\text{-}DFX}$ denote $EC_{50}$ and $E_{max}$ values of the standard agonist DFX (Table 1 and 2).

TABLE 1

HIF-1α transactivation assays in NIH-3T3-EPO Luc fibroblast cells. NIH3T3-EPO-luc cell line stably transfected with the Epo-Luc plasmid, which contains three copies of the Hypoxia Response Element consensus sequence from the promoter of the erythropoietin gene fused to luciferase gene. The efficacy and potency for HIF-1α activation is shown.

| Compound | Efficacy HIF-1α (IRA coefficient)[a] | Potency $EC_{50}$ HIF-1α (µM) |
|---|---|---|
| CBD | — | — |
| VCE-004 | — | — |
| II | 0.46 | 4.3 |

TABLE 1-continued

HIF-1α transactivation assays in NIH-3T3-EPO Luc fibroblast cells. NIH3T3-EPO-luc cell line stably transfected with the Epo-Luc plasmid, which contains three copies of the Hypoxia Response Element consensus sequence from the promoter of the erythropoietin gene fused to luciferase gene. The efficacy and potency for HIF-1α activation is shown.

| Compound | Efficacy HIF-1α (IRA coefficient)$^a$ | Potency $EC_{50}$ HIF-1α (μM) |
|---|---|---|
| III | 0.28 | 3.6 |
| IV | 0.61 | 3.2 |
| V | 0.85 | 1.8 |
| VI | 0.61 | 2.8 |
| VII | 0.68 | 2.9 |
| VIII | 0.63 | 2.6 |
| IX | 0.8 | 2.5 |
| X | 0.29 | 3.3 |

TABLE 2

HIF-1α transactivation assays in HaCaT-EPO Luc fibroblast cells. NIH3T3-EPO-luc cell line stably transfected with the Epo-Luc plasmid, which contains three copies of the Hypoxia Response Element consensus sequence from the promoter of the erythropoietin gene fused to luciferase gene. The efficacy and potency for HIF-1α activation is shown.

| Compound | Efficacy HIF-1α (IRA coefficient) | Potency $EC_{50}$ HIF-1α (μM) |
|---|---|---|
| CBD | — | — |
| VCE-004 | — | — |
| II | 3.87 | 3.2 |
| III | 5.84 | 1.7 |
| IV | 5.64 | 1.6 |
| V | 5.01 | 1.9 |
| VI | 3.02 | 4 |
| VII | 2.3 | 5.5 |
| VIII | 6.27 | 1.4 |
| IX | 8.64 | 1.4 |
| X | 10.35 | 1.2 |

A significant increase in luciferase activity was seen with all cannabinoid derivatives as compared with untreated cells. Thus, it can be concluded that the chemical modifications in position 3 of VCE-004 are critical to activate the HIF pathway.

Example 2. Cannabinoid Derivatives Stabilize the Levels of HIF-1α and HIF-2α in Different Cell Types and Inhibit PHDs Prolyl Hydrolase Activity To gain insight into the regulation of HIF-1α stabilization by the compounds of Formula (I), the effect on HIF-1α expression in different cell types was investigated. Human oligodendrocyte MO13.3 cells were stimulated for 6 h with either 150 μDFX or 1 μM of Cannabidiol (CBD). VCE-004, compounds II to V (FIG. 1A), compounds VI to X (FIG. 1B). After that, the cells were washed with PBS and incubated in 50 μl of NP-40 buffer (50 mM Tris-HCl pH 7.5, 150 mM NaCl, 10% glycerol and 1% NP-40) supplemented with 10 mM NaF, 1 mM $Na_3VO_4$, 10 μg/ml leupeptine. 1 μg/ml pepstatin and aprotinin, and 1 μl/ml PMSF saturated. After centrifugation, the supernatants were mixed with SDS sample buffer and boiled at 95° C. Proteins were electrophoresed in 8-10% sodium dodecyl sulfate polyacrylamide gel (SDS-PAGE) and transferred to polyvinylidene difluoride membranes (20 V and 30 min per membrane). After blocking with non-fat milk or BSA in TBST buffer, primary antibodies were added. The washed membranes were incubated with appropriate secondary antibodies coupled to horseradish peroxidase that were detected by an enhanced chemiluminescence system (USB). The antibody against HIF-1α (610959) was purchased from BD Biosciences and the antibody anti-β-tubulin (clone AA2) was purchased from Sigma-Aldrich (Saint Louis, Mo., USA).

All the compounds described in the present invention elevated HIF-lu protein level under normoxia conditions (21% $O_2$). The extent of induction was comparable to that of desferrioxamine (DFX), an iron chelator known to stabilize the levels of HIF-1α (FIGS. 1A and 1B).

Figure 2:
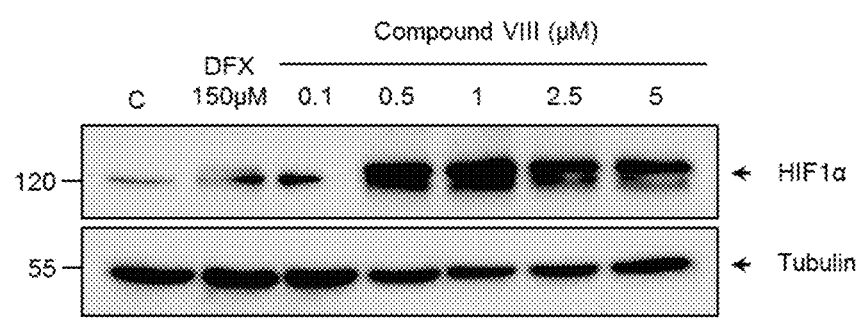
FIG. 2. HIF-1α level stabilization in oligodendrocytes.
Figure 2:
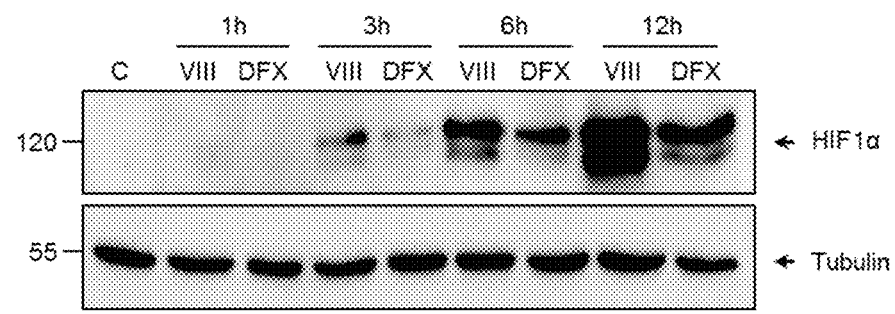

Next, MO13.3 cells (oligodendrocyte cell line) were stimulated with the increasing concentrations of compound VIII or with DFX (150 μM) during 6 h. After that, proteins isolation and western blots were performed as in FIG. 1. The results show that compound VIII induces stabilization of the levels of HIF-1α in a concentration dependent manner (FIG. 2A). FIG. 2B shows the time-course for stabilization of the levels of HIF-1α in MO13.3 treated with compound VIII.

The explanation to the stabilization of the levels of HIF-1α and HIF-2α proteins may be due to either the reduction of the expression of PHD proteins or the inhibition of its prolyl hydrolase activity. Thus, to identify which of said mechanisms is responsible for said stabilization, the expression of HIF-1α, HIF-2α and PDHs (PDH1, PDH2 and PDH3) proteins were analyzed by western blots. MO13.3 cells were stimulated with the increasing concentrations of compound VIII or with DFX (150 μM) during 6 h. After that, proteins isolation and western blots were performed as in FIG. 1. The antibodies anti-HIF-2α (ab8365), anti-PHD3 (ab30782) anti-PHD1 (ab80361) and anti-PHD2 (ab109088) were purchased from Abcam (Cambrigde, UK).

Figure 3:
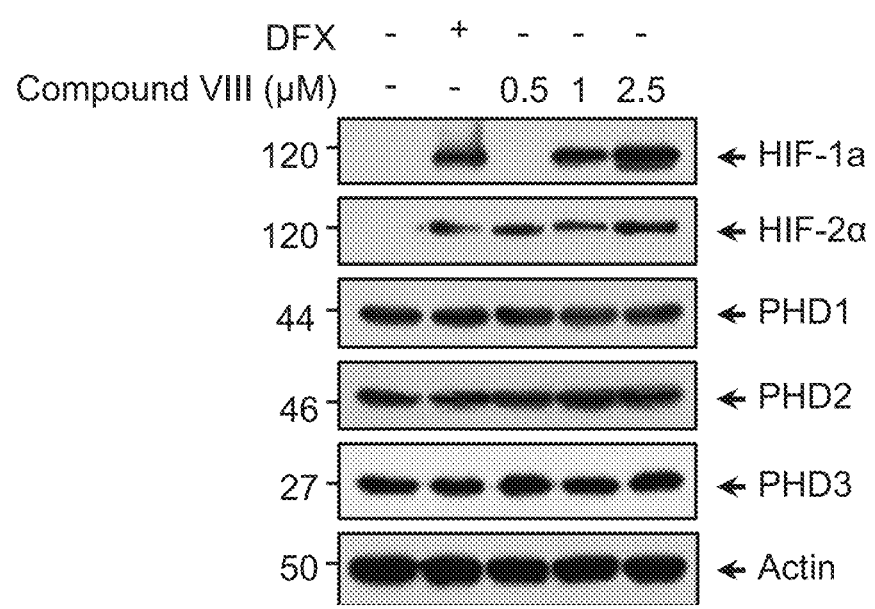
FIG. 3. HIF-1α and HIF-2α levels stabilization in oligodendrocytes. Stabilization of the levels of HIF-1α and HIF-2α induced by compound VIII without affecting the expression of PHDs. MO3.13 cells were stimulated with increasing concentrations of compound VIII or 150 µM of DFX during six hours. The steady state levels of the proteins HIF-1α, HIF-2α, PHD1, PHD2, PDH3, and actin, were determined by Western blots.

The results clearly show that compound VIII stabilized HIF-1α and HIF-2α expression without affecting the expression of PDH1, PDH2 and PDH3 (FIG. 3).

To study the activity of PDHs on the stabilization of the HIF-1α levels, MO13.3 cells were treated with increasing concentrations of compound VIII and the steady state levels of hydroxylated HIF-1α (OH-HIF-1α) and total HIF-1α proteins were identified by western blot.

Figure 4:
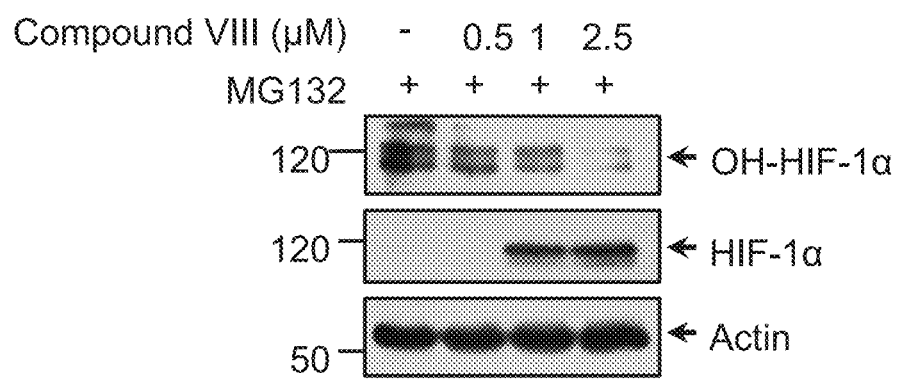
FIG. 4. Cannabidiol quinol derivatives Inhibit PHD activity. Inhibition of the HIF-1α hydroxylation activity of PHDs, and HIF-1α stabilization by compound VIII. MO3.13 cells were stimulated with increasing concentrations of compound VIII or 150 µM of DFX during six hours in the presence of the proteasome inhibitor MG132. The steady state levels of the proteins hydroxylated HIF-1α (OH-HIF-1α), HIF-1α, and actin, were determined by Western blots.

As depicted in FIG. 4 compound VIII led a decreased in the expression of OH-HIF-1α that paralleled with an increase in the expression of total HIF-1α protein.

Altogether, results indicate that compound VII inhibits the PDHs prolyl hydrolase activity and as consequence HIF-1α and HIF-2α protein levels are stabilized.

Figure 5:
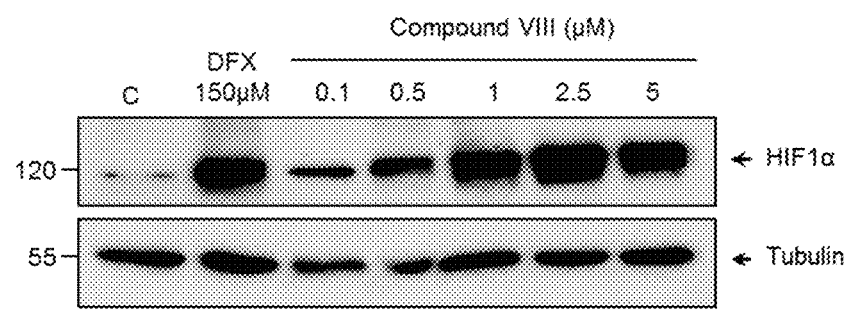
FIG. 5. HIF-1α and HIF-2α levels stabilization in Human Microvascular Endothelial Cells (HMEC).
Figure 5:
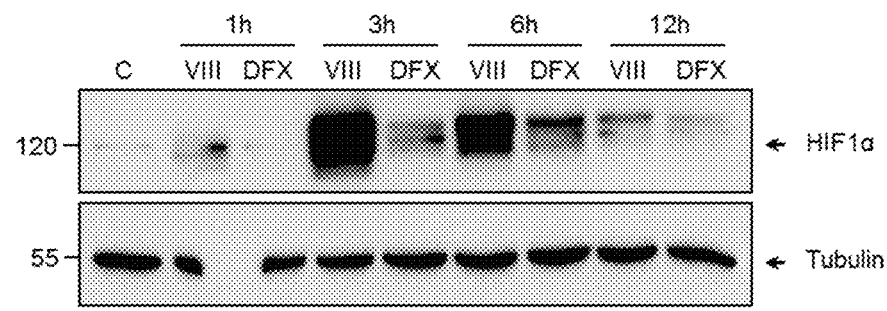
Figure 5:
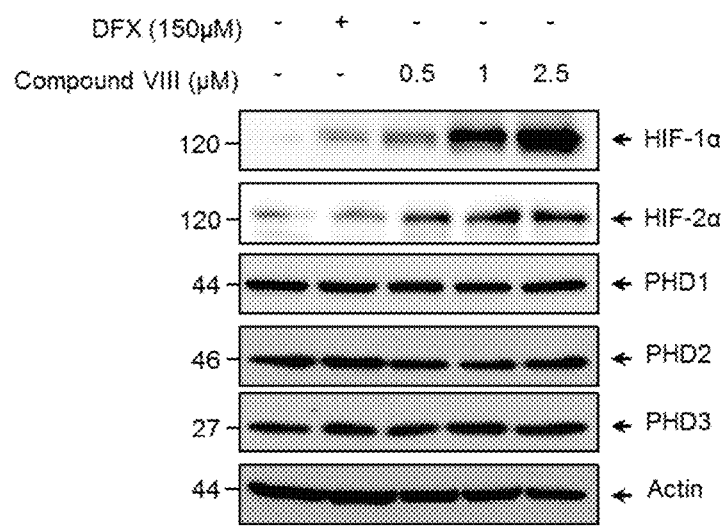
Figure 6:
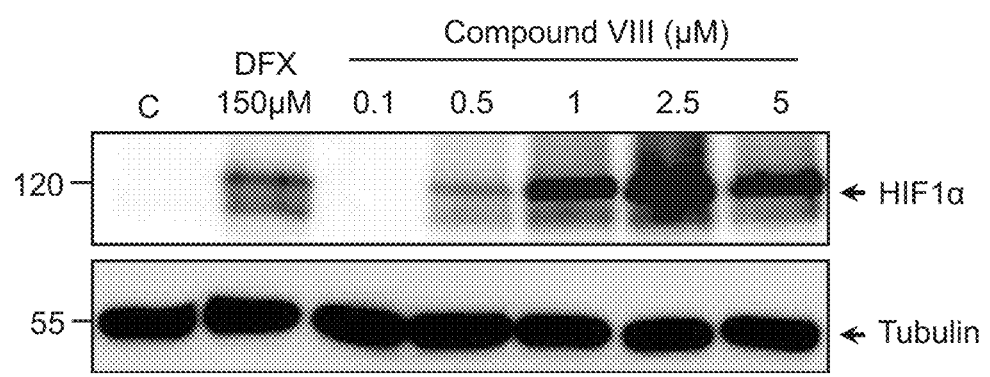
FIG. 6. HIF-1α level stabilization in neuronal cells. Stimulation of SK-N-SH cells with increasing concentrations of compound VIII or with DFX (150 µM) during 6 h. The steady state levels of the proteins HIF-1α and α-tubulin were determined by Western blots.

The stabilization of HIF-1α and HIF-2α protein levels by the compounds of Formula (I) was also shown in other cell types:

Human Microvascular Endothelial Cells (HMEC) were treated with increasing concentrations of compound VIII (FIG. 5A), and also treated with compound VIII (2.5 μM) at different times (FIG. 5B). It is shown that compound VIII induces the stabilization of HIF-1α levels in MO13.3 cells in a concentration dependent manner (FIG. 5A). Moreover, compound VIII also induces stabilization of the HIF-2α levels in this type of cells without affecting the expression of PDH1, PHD2 and PDH3 (FIG. 5C). It is also shown that the maximal expression of HIF-1α was achieved after 3 h of treatment with compound VIII (FIG. 5B). Similarly, compound VIII also induces stabilization of the levels of HIF-1α in SK-N-SH, a neuronal cell line (FIG. 6).

Example 3. Angiogenesis Induced by Compounds of Formula (I)

To test the functional consequences of compound VIII stimulation in a physiological model, endothelial cell tube formation was measured as a model of angiogenesis. CellPlayer™ GFP AngioKit-96 (Essen BioScience Inc., Welwyn Garden City, UK) was supplied as growing co-cultures of human matrix (normal human dermal fibroblast, NHDF) and endothelial cells (HUVEC) at the earliest stages of tubule formation. CellPlayer 96-well kinetic angiogenesis assay was performed according to the manufacturer's protocol. Briefly, lentivirally infected green fluorescent protein (GFP)-HUVECs were cocultured with normal human dermal fibroblasts in a 96-well microplate. The plate was placed in IncuCyte, and images were automatically acquired in both phase and fluorescence every 6 hours for 7 days. At day 1, compound VIII (1 µM) or rhVEGFA (10 ng/ml) were added on the endothelial tube networks and kept throughout the experiment. Tube formation over the 7-day assay was quantified using the Essen BioScience Angiogenesis Analysis Module. This module provides multiple assay metrics, including tube length and branch point formation, which are used to assess angiogenic effects on network formation. Briefly, the fluorescent images were analyzed to generate a segmentation mask closely resembling the in vitro network. The mask was then refined to specifically identify tube-forming events, and the kinetic response was plotted using the IncuCyte and GraphPad Prism software (La Jolla, Calif.).

Figure 7:
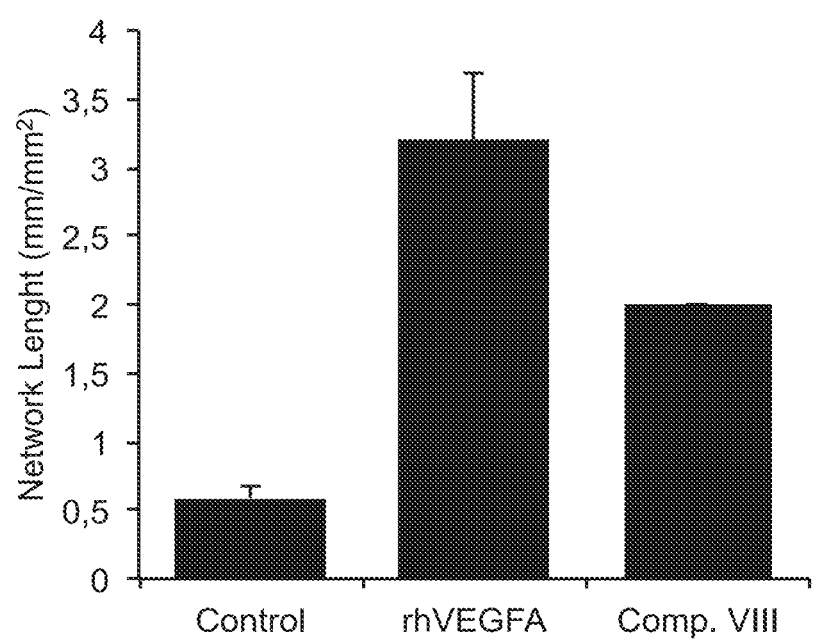
FIG. 7. Compound VIII Induces angiogenesis. Measurements of endothelial cell tube formation as a model of angiogenesis in green fluorescent Human endothelial vascular cells (HUVEC) co-cultured with primary fibroblasts and stimulated separately with compound VIII (1 µM) or VEGFA (10 ng/ml) for 7 days. Values of network length (in mm/mm$^2$) represent the mean±SEM (n=3).

In FIG. 7 it is shown that compound VIII 1 µM as well as the positive control VrhEGFA (10 ng/ml) increased significantly the network length in HUVEC cells.

Example 4. Compounds of Formula (I) Modulate the Expression of Genes Modulated by the HIF-1α Transcription Factor In order to understand the molecular mechanisms underlying the effects of compound VIII. HMEC cells were treated with compound VIII (5 µM) for 12 hours, and then mRNA was and the expression of 84 genes involved in the hypoxia was analyzed using the Human Hypoxia Signaling Pathway RT$^2$ Profiler PCR Array following the manufacturer's instructions (Qiagen Iberia, Madrid Spain). This array contains 84 key genes involved in fibrosis development. Data were analyzed using the $2^{-\Delta\Delta Ct}$ method and normalized with five housekeeping genes.

It is shown in Table 3 that compound VIII clearly upregulated the expression of a set of genes including ANGPTL4 and VEGFA that are known to be upregulated in response to hypoxia and in response to HIF PDHs inhibitors:

TABLE 3

Expression of HIF related genes in Human primary microvascular endothelial cells. Human primary microvascular endothelial cells were stimulated with compound VIII (5 µM) for 12 h and the expression analysis of genes involved in the human hypoxia-signaling pathway determined by PCR array. Gen Symbol, reference sequence number, description of each gene and fold induction or repression of gene expression compared to untreated control cells is shown. Refseq is referring to Human Hypoxia Signaling Pathway RT$^2$ Profiler PCR Array (Qiagen Iberia, Madrid Spain).

|     | Symbol | Refseq | Description | Fold Regulation (Comp. VIII 5 µm) |
| --- | --- | --- | --- | --- |
| A01 | ADM | NM_001124 | Adrenomedullin | 4.27 |
| A08 | BLM | NM_000057 | Bloom syndrome, RecQ helicase-like | −4.07 |
| B03 | EGLN1 | NM_022051 | Egl nine homolog 1 (C. elegans) | 4.25 |
| B05 | EGR1 | NM_001964 | Early growth response 1 | 7.09 |
| B09 | ERO1A | NM_014584 | ERO1-like (S. cerevisiae) | 5.60 |
| B12 | FOS | NM_005252 | FBJ murine osteosarcoma viral oncogene homolog | 8.04 |
| D01 | LOX | NM_002317 | Lysyl oxidase | 5.21 |
| D06 | MXI1 | NM_005962 | MAX interactor 1 | 5.69 |
| E01 | PDK1 | NM_002610 | Pyruvate dehydrogenase kinase, isozyme 1 | 4.89 |
| E03 | PFKFB3 | NM_004566 | 6-phosphofructo-2-kinase/fructose-2,6-biphosphatase | 8.56 |
| E09 | PLAU | NM_002658 | Plasminogen activator, urokinase | 6.86 |
| E12 | SERPINE1 | NM_000602 | Serpin peptidase inhibitor, clade E member 1 | 6.00 |
| F01 | SLC16A3 | NM_004207 | Solute carrier family 16, member 3 (monocarboxylic acid transporter 4) | 4.72 |
| F02 | SLC2A1 | NM_006516 | Solute carrier family 2 (facilitated glucose transporter), member 1 | 19.73 |
| F03 | TFRC | NM_003234 | Transferrin receptor (p90, CD71) | 3.26 |
| F09 | ALDOC | NM_005165 | Aldolase C, fructose-bisphosphate | 7.67 |
| F10 | ANGPTL4 | NM_001039667 | Angiopoietin-like 4 | 145.63 |
| F11 | ANKRD37 | NM_181726 | Ankyrin repeat domain 37 | 6.63 |
| F12 | BHLHE40 | NM_003670 | Basic helix-loop-helix family, member e40 | 8.22 |
| G01 | BNIP3 | NM_004052 | BCL2/adenovirus E1B 19 kDa interacting protein 3 | 6.46 |
| G02 | BNIP3L | NM_004331 | BCL2/adenovirus E1B 19 kDa interacting protein 3-like | 5.35 |
| G05 | HK2 | NM_000189 | Hexokinase 2 | 8.43 |
| G07 | NDRG1 | NM_006096 | N-myc downstream regulated 1 | 25.25 |
| G08 | P4HA1 | NM_000917 | Prolyl 4-hydroxylase, alpha polypeptide I | 10.56 |
| G09 | PFKFB4 | NM_004567 | 6-phosphofructo-2-kinase/fructose-2,6-biphosphatase 4 | 31.26 |
| G11 | SLC2A3 | NM_006931 | Solute carrier family 2 (facilitated glucose transporter), member 3 | 12.19 |
| G12 | VEGFA | NM_003376 | Vascular endothelial factor A | 18.09 |

To further extend the analysis of gene expression regulated by compounds of Formula (I), human brain microvascular cells (HBMEC) and MO13.3 cells were treated with increasing concentrations of compound VIII for 12 and the mRNA isolated. Single-stranded complementary DNA was synthesized from up to 1 µg of total RNA using iScript™ cDNA Synthesis Kit (Bio-Rad, Hercules, Calif., USA). The reaction mixture was kept frozen at −20° C. until enzymatic amplification. The iQ™ SYBR Green Supermix (Bio-Rad) was used to quantify mRNA levels for VEGFA and EPO. Real-time PCR was performed using a CFX96 Real-Time PCR Detection System (Bio-Rad). The GAPDH housekeeping gene was used to standardize the mRNA expression levels in every sample. Expression levels were calculated using the $2^{-\Delta\Delta Ct}$ method. Sequences of oligonucleotide primers are given in Table 4.

Figure 8:
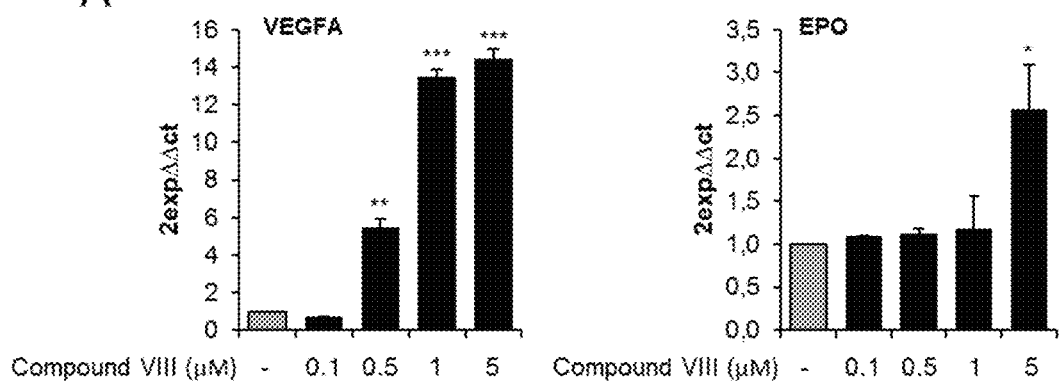
FIG. 8. Compound VIII induces the expression of the HIF-1α-dependent genes VGFA and EPO. MO13.3 cells (FIG. 8A) and HBMEC cells (FIG. 8B) were stimulated with increasing concentrations of compound VIII for 12 h and the expression of VGFA and EPO mRNAs determined by qPCR. Data are expressed as mean±SEM (n=3).
Figure 8:
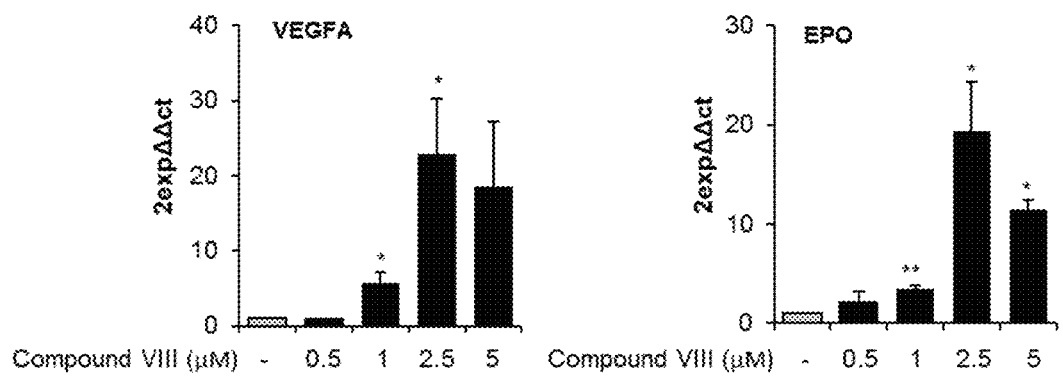

Compound VIII upregulated the expression of EPO and VEGFA in both MO13.3 and HBMEC cells (FIGS. 8A and 8B).

TABLE 4

List of human primer sequences used in quantitative Polymerase Chain Reaction.

| Gene | Forward | Reverse |
|------|---------|---------|
| EPO | 5'-ctccgaacaatcactgct-3' | 5'-ggtcatctgtccctgtcct-3' |
| VEGFA | 5'-cgaagtggtgaagttcatggatg-3' | 5'-ttctgtatcagtctttcctggtg-3 |
| GAPDH | 5'-tggcaaagtggagattgttgcc- -3' | 5'- aagatggtgatgggcttcccg-3' |

Example 5. Compounds of Formula (I) Induce Collagen Contraction

Figure 9:
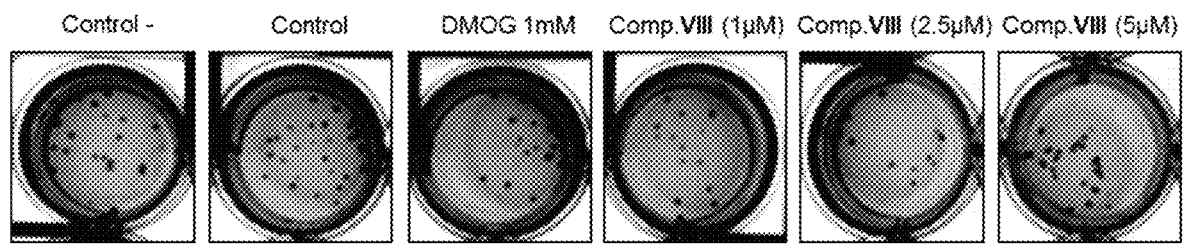
FIG. 9. Influence of compound VIII on collagen gel contraction. NIH 3T3-EPO-Luc fibroblasts were incorporated into collagen gels with and without indicated concentrations of compound VIII.
Figure 9:
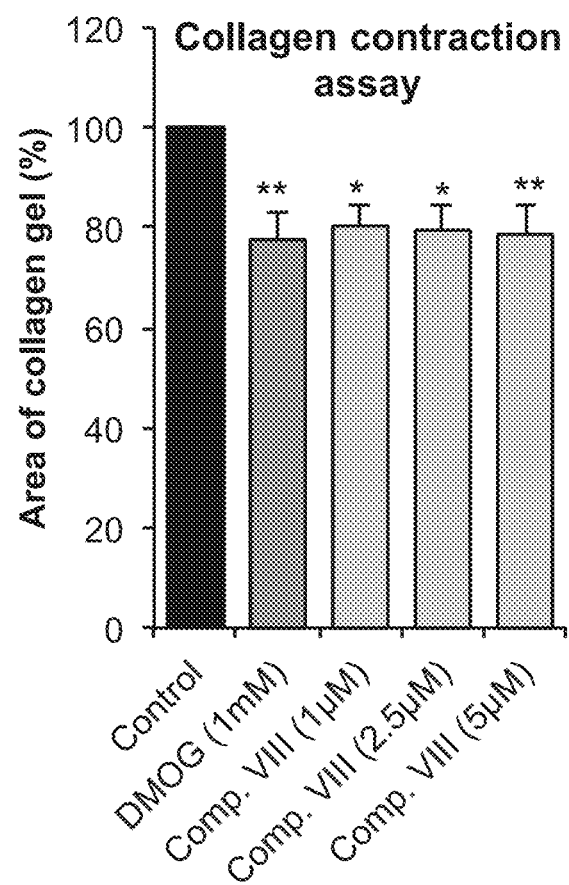

We explored whether the compounds of Formula (I) influence wound healing and tissue remodeling. For this purpose, a model of wound healing was used to assess the influence of compound VIII on fibroblast collagen gel contraction. NIH3T3-EPO-Luc were lifted from culture plates with trypsin, washed with PBS, and resuspended in complete medium at 500,000 cells/ml. Collagen gels were made as previously described (Phillips and Bonassar. Exp Cell Res. 2005, 310:79-87). All gels contained a final concentration of 150,000 cells/ml and 1.0 mg/ml collagen 1 with or without indicated concentrations of either compound VIII or 1 mM DMOG (dimethyloxaloylglycine). Gels were digitally imaged after release (t=0) and at various time points thereafter. Gel surface area was quantified in terms of pixel number using ImageJ (http://rsb.info.nih.gov/ij/). Relative changes in surface area are reported as a percent of the original surface area. As shown in FIG. 9 exposure of fibroblast embedded gels to compound VIII enhanced contraction of collagen gels to the same xtenet than DMOG, which was used as a positive control. These findings directly implicate compound VIII in tissue remodeling and wound contraction.

The present results substantiate the therapeutic use of the compounds described in the present inventions, for the clinical management of conditions that benefit from the inhibition of the PHDs activity or the stabilization of the HIF-1α and HIF-1β, such as stroke, traumatic injuries anemia, myocardial ischaemia-reperfusion injury, acute lung injury, infectious diseases, diabetic and chronic wounds, organ transplantation, acute kidney injury and arterial diseases.

The invention claimed is:

1. A method of treating a condition that benefits from the inhibition of the hypoxia-inducible factor (HIF) propyl hydroxylases (PDHs) activity, wherein the condition that benefits from the inhibition of the HIF PHDs activity is independently selected from the group consisting of stroke, traumatic injuries, anemia, myocardial ischaemia-reperfusion injury, acute lung injury, diabetic and chronic wounds, organ transplantation, acute kidney injury, and arterial diseases; the method comprising administering a compound of Formula (I), or pharmaceutically acceptable salts thereof,

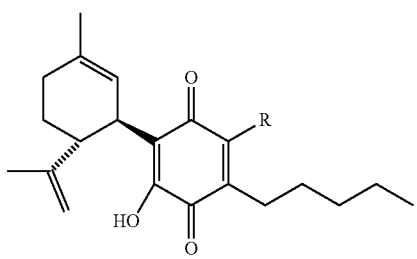

(I)

to a subject in need thereof,
wherein R is the carbon atom of a group, represented by aryl, linear or branched alkenyl, linear or branched alkynyl, acyl, or alkoxycarbonyl groups; or
wherein R is the nitrogen atom of a group, represented by linear or branched alkylamine, an arylamine, a linear or branched alkenylamine or a linear or branched alkynylamine.

2. The method of claim 1, wherein R is the nitrogen of a group, represented by a linear or branched alkylamine, an arylamine, a linear or branched alkenylamine or a linear or branched alkynylamine.

3. The method of claim 1, wherein the compound of Formula (I) is independently selected from the group consisting of:

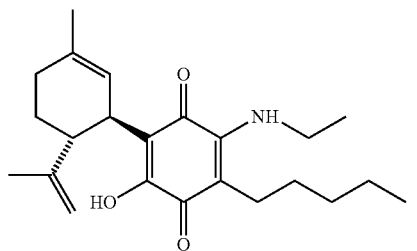

(II)

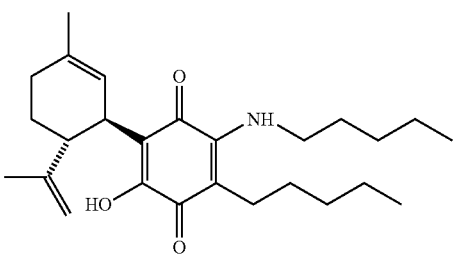

(III)

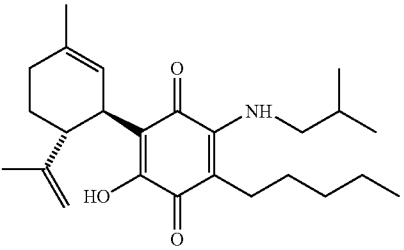

(IV)

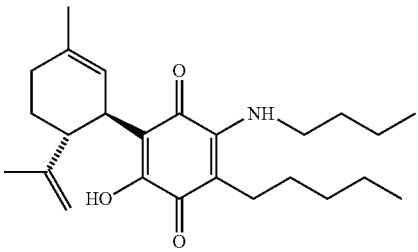

(V)

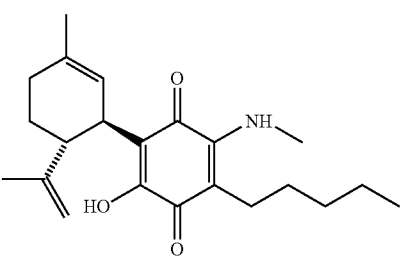

(VI)

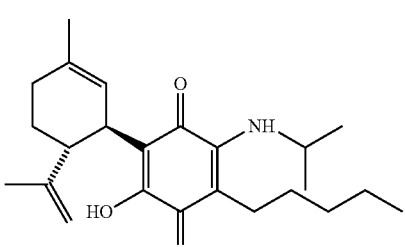

(VII)

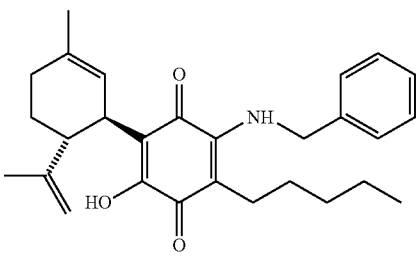

(VIII)

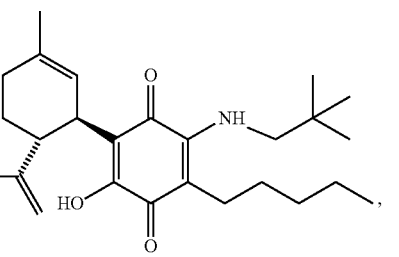

(IX)

, and

-continued
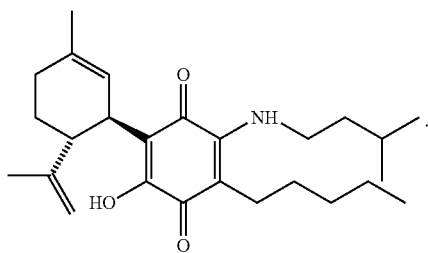
(X)
4. The method of claim 1, wherein the condition that benefits from the inhibition of the HIF PHDs activity is stroke.
5. The method of claim 3, wherein the condition that benefits from the inhibition of the HIF PHDs activity is stroke.
6. The method of claim 5, wherein the compound of Formula (I) is a compound of Formula (VIII)
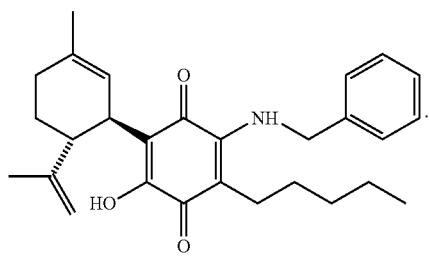
(VIII)
* * * * *

UNITED STATES PATENT AND TRADEMARK OFFICE
CERTIFICATE OF CORRECTION

PATENT NO. : 10,919,843 B2
APPLICATION NO. : 16/498768
DATED : February 16, 2021
INVENTOR(S) : Eduardo Muñoz Blanco et al.

It is certified that error appears in the above-identified patent and that said Letters Patent is hereby corrected as shown below:

In the Claims

Column 31, Claim 1, Line 3 currently recites:
- inhibition of the hypoxia-inducible factor (HIF) propyl -
But should be corrected to:
- inhibition of the hypoxia-inducible factor (HIF) prolyl -

Column 31, Claim 1, Line 4 currently recites:
- hydroxylases (PDHs) activity, wherein the condition that -
But should be corrected to:
- hydroxylases (PHDs) activity, wherein the condition that -

Signed and Sealed this
Twenty-third Day of July, 2024

Katherine Kelly Vidal
*Director of the United States Patent and Trademark Office*